United States Patent [19]

Weber et al.

[11] Patent Number: 5,688,789
[45] Date of Patent: Nov. 18, 1997

[54] PCP RECEPTOR LIGANDS AND THE USE THEREOF

[75] Inventors: Eckard Weber, Laguna Beach, Calif.; John F. W. Keana, Eugene, Oreg.; Peter Barmettler, Andover, Mass.

[73] Assignee: State of Oregon, acting by and through the Oregon State Board of Higher Education, acting for and on behalf of the Oregon Health Sciences University and the University of Oregon, Eugene, Oreg.

[21] Appl. No.: 450,155

[22] Filed: May 26, 1995

Related U.S. Application Data

[63] Continuation of Ser. No. 875,787, Apr. 29, 1992, which is a continuation-in-part of Ser. No. 693,244, Apr. 29, 1991, abandoned, which is a continuation-in-part of Ser. No. 337,858, Apr. 14, 1989, Pat. No. 5,011,834.

[51] Int. Cl.$^6$ .................... A61K 31/55; C07D 471/08
[52] U.S. Cl. ............................................. 514/214; 540/581
[58] Field of Search ........................ 514/212, 214; 540/581, 281

[56] References Cited

U.S. PATENT DOCUMENTS

| | | | |
|---|---|---|---|
| 3,310,565 | 3/1967 | Galantay | 260/288 |
| 3,361,767 | 1/1968 | Dobson et al. | 260/343.2 |
| 3,403,156 | 9/1968 | Humber et al. | 260/286 |
| 3,403,157 | 9/1968 | Himber et al. | 260/288 |
| 3,426,015 | 2/1969 | Dobson et al. | 260/239.3 |
| 3,458,518 | 7/1969 | Dobson et al. | 260/286 |
| 3,487,075 | 12/1969 | Davis et al. | 260/239.3 |
| 3,491,088 | 1/1970 | Dobson et al. | 260/239.3 |
| 3,493,560 | 2/1970 | Dobson et al. | 260/239.3 |
| 3,509,134 | 4/1970 | Davis et al. | 260/239.3 |
| 3,542,787 | 11/1970 | Dobson et al. | 260/286 |
| 3,597,433 | 8/1971 | Dobson et al. | 260/286 R |
| 3,641,038 | 2/1972 | Davis et al. | 260/289 R |
| 3,716,541 | 2/1973 | Dobson et al. | 260/286 R |
| 3,717,641 | 2/1973 | Kocsis et al. | 260/286 R |
| 3,812,119 | 5/1974 | Walker | 260/247 |
| 3,892,756 | 7/1975 | Nedelec et al. | 260/289 C |
| 4,009,273 | 2/1977 | Nedelec et al. | 424/258 |
| 4,052,508 | 10/1977 | Anderson et al. | 424/258 |
| 4,064,139 | 12/1977 | Anderson et al. | 260/313.1 |
| 4,148,898 | 4/1979 | Koch et al. | 424/256 |
| 4,232,158 | 11/1980 | Shepard et al. | 546/72 |
| 4,374,838 | 2/1983 | Anderson et al. | 424/256 |
| 4,399,141 | 8/1983 | Anderson et al. | 424/256 |
| 4,465,677 | 8/1984 | DeMarinis et al. | 424/244 |
| 4,762,828 | 8/1988 | Georgiev et al. | 514/214 |
| 4,789,673 | 12/1988 | Donatsch et al. | 514/214 |
| 4,888,347 | 12/1989 | Woodruff et al. | 514/289 |
| 4,940,789 | 7/1990 | Childers, Jr. et al. | 540/581 |
| 5,011,834 | 4/1991 | Weber et al. | 514/212 |
| 5,196,415 | 3/1993 | Monn et al. | 514/210 |

FOREIGN PATENT DOCUMENTS

| | | |
|---|---|---|
| 0 091 071 | 10/1983 | European Pat. Off. . |
| 0 230 370 | 7/1987 | European Pat. Off. . |
| 1 035 141 | 7/1958 | Germany . |
| 485654 | 3/1970 | Switzerland . |
| 510684 | 9/1971 | Switzerland . |
| 1146109 | 3/1969 | United Kingdom . |
| 1146110 | 3/1969 | United Kingdom . |
| 1 336 634 | 11/1973 | United Kingdom . |
| WO 90/12575 | 11/1990 | WIPO . |

OTHER PUBLICATIONS

Battesby et al., *J. Chem. Soc.*, pp. 1988–1991 (1958).
Brooks et al., *J.C.S. Perkin 1*, No.21, pp. 2588–2591 (1973).
Brown et al., *Tetrahedron Letters*, No. 19, pp. 1515–1517 (1969).
Christy et al., *J. Org. Chem.*, 44(18):3117–3127 (1979).
Cioranescu et al., *Revue Toumaine de Chimie*, 16(10):1555–1566 (1971).
Dobson et al., *Tetrahedron Letters*, No. 42, pp. 4139–4142 (1967).
Dobson et al., *Can. J. Chem.*, 49:1027–1031 (1971).
Drejer et al., *European Journal of Pharmacology*, 143:287–290 (1987).
Dygos, *J. Heterocyclic Chem.*, 13:1355–1357 (1976).
Dyke et al., *Tetrahedron*, 28:2999–4001 (1972).
Evans et al., *J. Org. Chem.*, 44(18):3127–3135 (1979).
Gootjes et al., *Arzeim.-Forsch. (Drug Res.)*, 22(3):632–634 (1972).
Reden et al., *Adv. Exp. Med. Biol.*, 126:69–72 (1980).
Rice et al., *J. Org. Chem.*, 45:601–607 (1980).
Russel et al., *Chem. Abstr.*, 71:285–286, No. 30370d (1969).
Slavik et al., *Romeria refracta. Collection Czechoslov. Chem. Commun.*, 33:4066–4082 (1968).
Takayama et al., *Heterocycles*, 9(11):1545–1548 (1978).
Vanderlaan et al., *J. Org. Chem.*, 50:743–747 (1985).
Waldmann et al., *Ann.*, 609:125–143 (1957).
Walker et al., *J. Org. Chem.*, 36(3):466–478 (1971).
Weber et al., *Chem. Abstr.*, 115:76, No. 106019w (1991).
*The Merck Manual*, 15th ed. (1987), Berkow, M.D. editor, 2399–2400.
*Remington's Pharmaceutical Sciences*, 18th ed. (1990), pp. 625–628, 632.
*Cecil Textbook of Medicine, 19th edition*, Wyngaarden, M.D. editor, pp. 2075–2078, 2135–2136, 2141–2142 (1992).
*Physicians' Guide To Rare Diseases*, Thoene, M.D. editor, pp. 55–56 (1992).

*Primary Examiner*—Mark L. Berch
*Assistant Examiner*—Bruck Kifle
*Attorney, Agent, or Firm*—David G. Conlin; Peter F. Corless

[57] ABSTRACT

The invention relates to 5-(iminomethano)-10,11-dihydro-5H-dibenzo[a,d]cycloheptene and derivatives thereof. The invention also relates to the use of such compounds for the treatment or prevention of neuronal loss in ischemia, hypoxia, brain or spinal chord trauma, as well as for the treatment of Alzheimer's disease, amyotrophic lateral sclerosis, Huntington's disease and Down's syndrome.

23 Claims, 2 Drawing Sheets

PCP RECEPTOR LIGANDS AND THE USE THEREOF

CROSS REFERENCE TO RELATED APPLICATIONS

The present application is a continuation of application Ser. No. 07/875,787, filed Apr. 29, 1992, which is a continuation-in-part of U.S. application Ser. No. 07/693,244, filed Apr. 29, 1991, abandoned, which is a continuation-in-part of U.S. application Ser. No. 07/337,858, filed Apr. 14, 1989, corresponding to U.S. Pat. No. 5,011,834, issued Apr. 30, 1991, the contents of which are fully incorporated by reference herein.

The government has certain rights in this invention pursuant to Grant Nos. MH40403 and MH42068.

FIELD OF THE INVENTION

The invention is in the field of pharmaceutical compositions which are useful for the prevention and/or treatment of neurodegradation and other neuropathological conditions in animals.

BACKGROUND OF THE INVENTION

The amino acid L-glutamate is widely thought to act as a chemical transmitter substance at excitatory synapses within the central nervous system. Neuronal responses to glutamate are complex and appear to be mediated by at least three different receptor types, i.e., KA, QA and NMDA subtypes, each being named for their relatively specific ligands, i.e., kainic acid, quisqualic acid and N-methyl-D-aspartic acid, respectively.

NMDA receptors are strongly involved in nerve cell death which occurs following brain ischemia or hypoxia. Upon the occurrence of ischemic/hypoxic brain insults such as those which occur during spinal or head trauma, stroke or heart attack, an excessive release of endogenous glutamate occurs from nerve terminals deprived of the energy supplies needed to retain the neurotransmitter. The excessive amounts of glutamate cause an over-stimulation of NMDA receptors on nearby neurons. Associated with the NMDA receptors is an ion channel. The recognition site, i.e., the NMDA receptor, is external to the ion channel. When glutamate interacts with the NMDA receptor, it causes the ion channel to open, thereby permitting a flow of cations across the cell membrane, e.g., $Ca^{2+}$ and $Na^+$ into the cell and $K^+$ out of the cell. It is believed that this flux of ions, especially the influx of $Ca^{2+}$ ions, caused by the interaction of glutamate with the NMDA receptor plays an important role in neuronal death. See, e.g., Rothman, S. M. and Olney, J. W., Trends in Neurosci. 10(7):299–302 (1987).

Agents which block responses to NMDA receptor activation therefore have potential therapeutic uses in the treatment of neurological disorders and nerve cell death resulting from hypoxia or hypoglycemia or following brain ischemia which occurs during stroke, trauma and heart attack. A number of disorders of the nervous system are associated with neurodegeneration that may be caused by over-activation of NMDA receptors. Antagonists of NMDA receptor-mediated responses have potential therefore for the treatment of such disorders as Alzheimer's disease, Huntington's chorea, amyotrophic lateral sclerosis and Down's Syndrome.

Research on the NMDA receptor-ion channel complex has led to the determination of a receptor site within the ion channel known as the PCP receptor. See Vincent, J. P., Kartalovski, B., Geneste, P., Kamenka, J. M. and Lazdunski, M., Proc. Natl. Acad. Sci. USA 76:4678–4682 (1979); Zukin, S. R. and Zukin, R. S., Proc. Natl. Acad. Sci. USA 76:5372–5376 (1979); Sonders, M. S., Keana, J. F. W. and Weber, E., Trends in Neurosci. 11(1):37–40 (1988); and Anis, N. A., Berry, S. C., Burton, N. R. and Lodge, D., Br. J. Pharmacol. 79:565–575 (1983). Compounds which bind to the PCP receptor can act as ion channel blockers, thereby interrupting the flow of ions across the cell membrane. In this manner, agents which interact with the PCP receptor act as non-competitive blockers, reducing the agonist action of glutamate at the NMDA receptor.

Known PCP receptor ligands include PCP [angel dust], i.e., phencyclidine, analogues such as 1-[1-(2-thienyl)-cyclohexyl]-piperidine (TCP), benzomorphan (sigma) opiates, dioxolanes and 5-methyl- 10,11-dihydro-5H-dibenzo[a,d]cycloheptene-5,10-imine (i.e., the drug MK-801, see U.S. Pat. No. 4,399,141). See, also, Wong, E. H. F., Kemp, J. A., Priestly, T., Knight, A. R., Woodruff, G. N., and Iversen, L. I., Proc. Natl. Acad. Sci. USA 83:7104–7108 (1986). MK-801 is apparently the most potent selective PCP receptor ligand/NMDA channel blocker known to date.

European Patent Application Publication No. 0230370, Published Jul. 29, 1987, discloses compounds having the Formula(I):

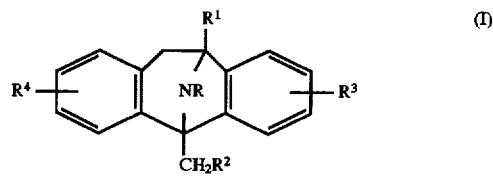

Where $R^1$, $R^2$, $R^3$, and $R^4$ are H, the compound is MK-801. This compound and derivatives thereof are the subject of a patent to Anderson et al, U.S. Pat. No. 4,399,141 (1983).

U.S. Pat. No. 4,374,838 to Anderson et al. (1983) discloses compounds related to MK-801 of the Formula (II):

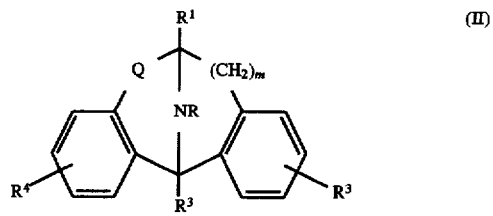

which are useful as muscle relaxants, antidepressants, anticonvulsants, and in the treatment of mixed anxiety-depression, minimal brain dysfunction, and extrapyramidal disorders.

U.S. Pat. No. 4,064,139 to Anderson et al. (1977) discloses compounds related to MK-801 of Formula (III):

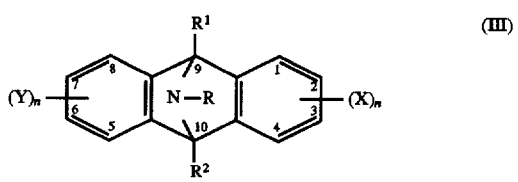

which are useful as minor tranquilizers, anticonvulsants, muscle relaxants, and in the treatment of extrapyramidal disorders such as Parkinson's disease.

U.S. Pat. No. 3,509,158 to Dobson et al. (1970) discloses 10,5-(iminomethano)-10,11-dihydro-5H-dibenzo[a,d]- cycloheptene and derivatives thereof of the Formula (IV):

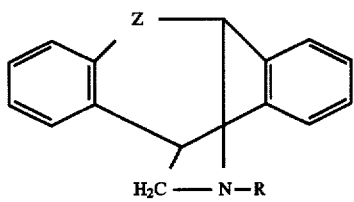

wherein Z represents a group selected from the group consisting of

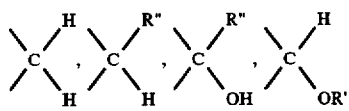

These compound are reportedly useful as trichomonacidal, anticonvulsant, anti-parasitic, anti-inflammatory and hypotensive agents.

U.S. Pat. No. 4,232,158 to Shepard et al. (1980), discloses 10,11-dihydro-5H-dibenzo[a,d]cyclohepten-5,10-imines and derivatives thereof having the following structural Formula (V):

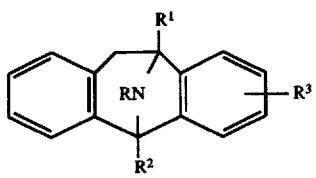

These compounds are reported useful as anti-anxiety agents, as muscle relaxants and in the treatment of extrapyramidal disorders such as Parkinson's disease.

U.S. Pat. No. 3,641,038 to Davis et at (1972), discloses 10,11-dihydro-10,5-(iminomethano)-5H-dibenzo[a,d]-cyclohepten-10-ol derivatives having the Formula (VI):

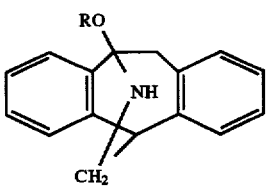

These compounds reportedly possess anti-convulsant activities.

U.S. Pat. No. 3,542,787 to Dobson et al. (1970), discloses 10,11-dihydro-5,10-(iminomethano)-5H-dibenzo[a,d]-cycohepten-13-imine having the Formula (VII):

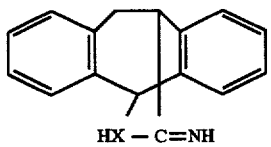

This compound reportedly has hypotensive properties.

U.S. Pat. No. 3,597,433 to Dobson et al. (1971), discloses 10,11-dihydro-5,10-(iminomethano)-5H-dibenzo[a,d]-cycloheptene and its derivatives having the following Formula (VIII):

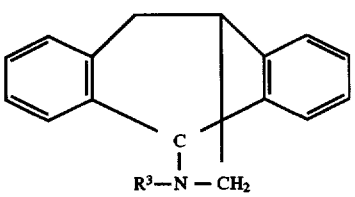

These compounds reportedly have anticonvulsant activity substantially free from ataxic side-effects.

U.S. Pat. No. 3,716,541 to Dobson et al. (1973), discloses 11-substituted derivatives of 10,11-dihydro-5,10-(iminomethano)-5H-dibenzo[a,d]-cycloheptene having the Formula (IX):

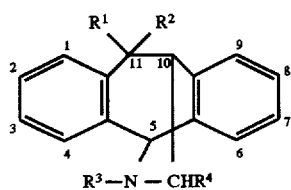

The compounds reportedly exhibit central nervous system depressant and anticonvulsant properties without causing ataxia.

U.S. Pat. No. 3,717,641 to Kocsis et al. (1973), discloses 5,6,11,12-tetrahydrodibenzo[a,e]cycloocten-5,11-imine having the Formula (x):

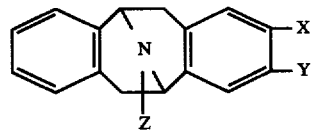

These compounds reportedly have anti-tussive and musculotropic spasmolytic activities.

U.S. Pat. No. 3,892,756 to Nedelec et al. (1975), discloses 5,10-imino-dibenzo-cycloheptenes having the Formula (XI):

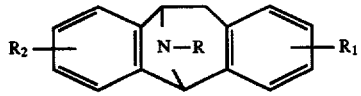

These compounds are reportedly useful as stimulants and anticonvulsants.

U.S. Pat. No. 4,009,273 to Nedelec et al. (1977), discloses compounds of the Formula (XII):

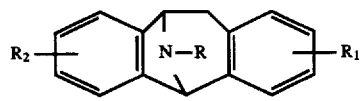

These compounds are reportedly useful as stimulants and anticonvulsants.

U.S. Pat. No. 4,052,508 to Anderson et al. (1977), discloses dihydroanthracen imines and derivatives thereof having the Formula (XIII):

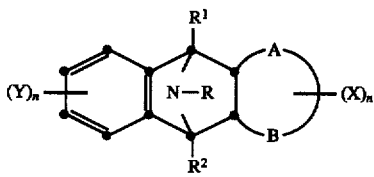

(XIII)

These compounds are reportedly useful as minor tranquilizers, anticonvulsants, muscle relaxants, and in the treatment of extrapyramidal disorders such as Parkinson's disease.

U.S. Pat. No. 4,064,139 to Anderson et al. (1977), discloses substituted 9,10-dihydroanthracene-9,10-imines having the Formula (XIV):

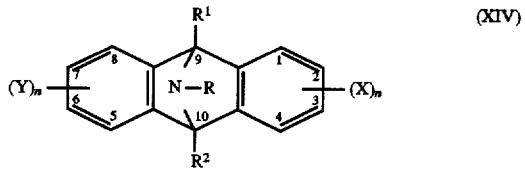

(XIV)

These compounds are reportedly useful as minor tranquilizers, anticonvulsants, muscle relaxants, and in the treatment of extrapyramidal disorders such as Parkinson's disease.

Despite the development of the above-mentioned derivatives, a need continues to exist for new methods for the treatment or prevention of neuronal loss associated with stroke, ischemia, CNS trauma, and hypoglycemia, as well as for the treatment or prevention of neurodegenerative diseases including Alzheimer's disease, amyotrophic lateral sclerosis, Huntington's disease, and Down's syndrome.

SUMMARY OF THE INVENTION

The invention relates to a method of treating or preventing neuronal loss associated with stroke, ischemia, CNS trauma, and hypoglycemia, as well as treating neurodegenerative diseases including Alzheimer's disease, amyotrophic lateral sclerosis, Huntington's disease and Down's syndrome, comprising administering to an animal in need of such treatment a compound of the Formula (XVI):

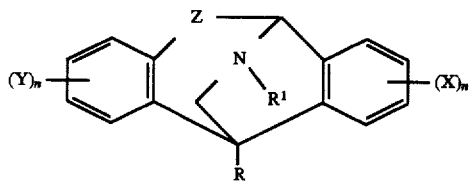

(XVI)

wherein:

R is hydrogen, $C_2$–$C_6$ acyl, $C_1$–$C_6$ alkyl, aryl, $C_1$–$C_6$ alkoxycarbonyl, $C_7$–$C_{10}$ aralkyl, $C_2$–$C_6$ alkenyl, $C_3$–$C_{15}$ dialkylaminoalkyl, $C_1$–$C_6$ hydroxyalkyl, $C_2$–$C_6$ alkynyl, $C_3$–$C_{15}$ trialkylsilyl, $C_4$–$C_{10}$ alkylcycloalkyl, or $C_3$–$C_6$ cycloalkyl;

$R^1$ is hydrogen, $C_1$–$C_6$ alkyl, $C_2$–$C_6$ alkenyl, $C_7$–$C_{10}$ aralkyl, $C_1$–$C_6$ alkoxy, $C_1$–$C_6$ alkylamino or $C_3$–$C_{15}$ dialkylaminoalkyl;

X and Y are independently selected from the group consisting of a halogen such as chloro, fluoro, bromo, iodo, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, e.g. trifluoromethyl; $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, $C_5$–$C_6$ heterocycloalkyl, $C_1$–$C_6$ alkylthio, $C_{1-6}$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_{1-6}$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl;

Z represents a group selected from

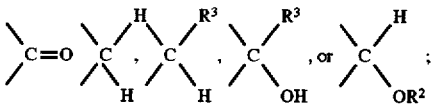

wherein $R^2$ is hydrogen, $C_1$–$C_6$ alkyl, $C_2$–$C_6$ alkenyl, aralkyl, $C_4$–$C_{15}$ dialkylaminoalkyl, heterocycloalkyl, $C_2$–$C_6$ acyl, aroyl, or aralkanoyl, and $R^3$ is $C_1$–$C_6$ alkyl, $C_2$–$C_6$ alkenyl, phenyl, aralkyl or $C_3$–$C_{15}$ dialkylaminoalkyl; and n is an integer selected from 0 (X or Y is hydrogen, respectively), 1, 2, 3, or 4;

or a pharmaceutically acceptable salt thereof;

wherein said compound exhibits a high binding activity with respect to the PCP receptor in mammalian nerve cells, and is administered is present in an amount effective to treat or prevent said neuronal loss or to treat said disease.

DESCRIPTION OF THE PREFERRED EMBODIMENTS

Figure 1:
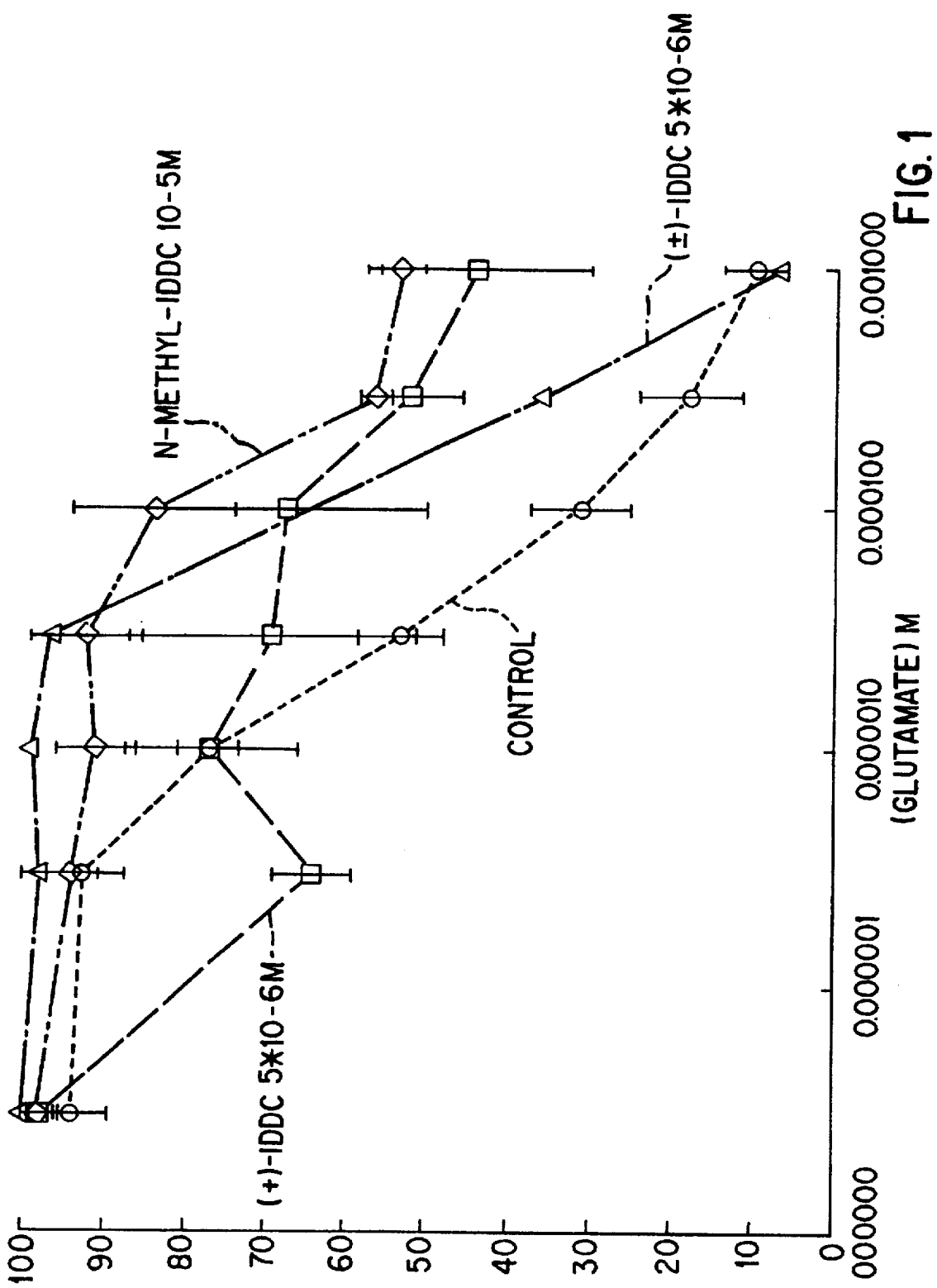
FIG. 1 depicts a graph showing the in vitro neuroprotective effect of (±) 10,5-(iminomethano)-10,11-dihydro-5H-dibenzo[a,d]cycloheptene (IDDC), (+) IDDC, N-methyl IDDC and a control sample on rat hippocampal cells treated with various concentrations of glutamate.

The invention relates to a method of treating or preventing neuronal loss associated with stroke, ischemia, CNS trauma, and hypoglycemia, as well as treating neurodegenerative diseases including Alzheimer's disease, amyotrophic lateral sclerosis, Huntington's disease, and Down's syndrome, comprising administering to an animal, i.e. a human, in need of such treatment a compound of the Formula (XVI):

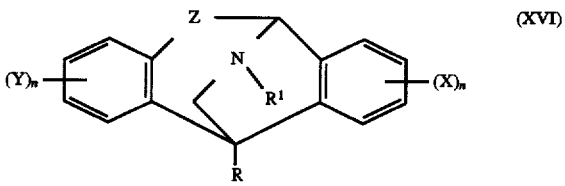

(XVI)

wherein:

R is hydrogen, $C_2$–$C_6$ acyl, $C_1$–$C_6$ alkyl, aryl, $C_1$–$C_6$ alkoxycarbonyl, $C_7$–$C_1$ aralkyl, $C_2$–$C_6$ alkenyl, $C_3$–$C_{15}$ dialkylaminoalkyl, $C_1$–$C_6$ hydroxyalkyl, $C_2$–$C_6$ alkynyl, $C_3$–$C_{15}$ trialkylsilyl, $C_4$–$C_{10}$ alkylcycloalkyl, or $C_3$–$C_6$ cycloalkyl;

$R^1$ is hydrogen, $C_1$–$C_6$ alkyl, $C_2$–$C_6$ alkenyl, $C_7$–$C_{10}$ aralkyl, $C_1$–$C_6$ alkoxy, $C_1$–$C_6$ alkylamino, or $C_3$–$C_{15}$ dialkylaminoalkyl;

X and Y are independently selected from the group consisting of a halogen such as chloro, fluoro, bromo, iodo, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, e.g. trifluoromethyl; $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl;

Z represents a group selected from

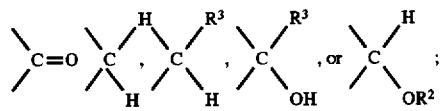

wherein $R^2$ is hydrogen, $C_1$–$C_6$ alkyl, $C_2$–$C_6$ alkenyl, aralkyl, $C_4$–$C_{15}$ dialkylaminoalkyl, heterocycloalkyl, $C_2$–$C_6$ acyl, aroyl, or aralkanoyl, and $R^3$ is $C_1$–$C_6$ alkyl, $C_2$–$C_6$ alkenyl, phenyl, aralkyl or $C_3$–$C_{15}$ dialkylaminoalkyl; and n is an integer selected from 0 (X or Y is hydrogen, respectively), 1, 2, 3 or 4, or a pharmaceutically acceptable salt thereof;

wherein said compound exhibits a high binding activity with respect to the PCP receptor in mammalian nerve cells, and is administered in an The compounds having Formula (XVI) above may exist in racemic form or in the optically active stereoisomeric form. In addition, the compounds having Formula (XVI) may exist in radiolabeled form, e.g. wherein the one or more of the atoms are substituted by $^3H$, $^{11}C$, $^{14}C$, $^{18}F$, $^{15}N$, $^{125}I$, $^{131}I$, $^{35}S$ or $^{32}P$.

Preferably, the compounds of the invention are those of Formula (XVI) wherein R is H, i.e., those having the following structural Formula (XVII):

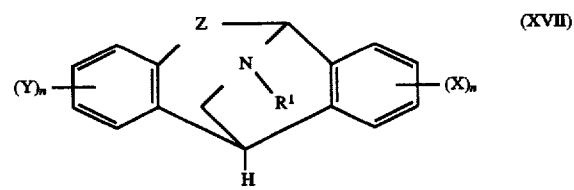

wherein $R^1$, X, Y, Z and n are as defined above.

Typical $C_1$–$C_6$ alkyl groups include methyl, ethyl, n-propyl, i-propyl, n-butyl, t-butyl, i-butyl, pentyl, i-pentyl and hexyl groups.

Typical $C_2$–$C_6$ acyl groups include acetyl, propanoyl, i-propanoyl, butanoyl, s-butanoyl, pentanoyl and hexanoyl groups.

Typical aryl groups include phenyl, naphthyl, phenanthryl and anthracyl groups.

Typical $C_1$–$C_6$ alkoxycarbonyl groups include carbonyl substituted by methoxy, ethoxy, propanoxy, i-propanoxy, n-butanoxy, t-butanoxy, i-butanoxy, pentanoxy, and hexanoxy groups.

Typical aralkyl groups include the above-listed $C_1$–$C_6$ alkyl groups substituted by phenyl, naphthyl, phenanthryl and anthracyl groups, e.g. benzyl, phenethyl, phenylpropyl, phenylisopropyl, and phenylbutyl.

Typical $C_2$–$C_6$ alkenyl groups include vinyl, allyl, 2-butenyl, 2-pentenyl, and 2-hexenyl groups.

Typical $C_2$–$C_6$ alkynyl groups include ethynyl and propargyl groups.

Typical halo groups include fluorine, chlorine, bromine and iodine.

Typical $C_2$–$C_6$ alkynyl groups include acetynyl and propargyl groups.

Typical halo groups include fluorine, chlorine, bromine and iodine.

Typical aroyl groups include carbonyl substituted by phenyl, naphthyl, phenanthryl and anthracyl groups.

Typical aralkanoyl groups include carbonyl substituted by the above-listed aralkyl groups.

Typical aralkoxy groups include the above listed $C_1$–$C_6$ alkoxy groups substituted by phenyl, naphthyl, phenanthyl and anthracyl groups.

Typical substituted aryl groups include the above-listed aryl groups substituted by halo, hydroxy, amino, and the like.

Typical heteroaryl groups include furyl, thienyl, pyrrolyl, thiazolyl, pyridyl, pyrimidinyl, pyrizinyl and oxazolyl groups.

Typical substituted heteroaryl groups include the above-listed heteroaryl groups substituted by halo, $C_1$–$C_6$ alkyl and the like.

Typical $C_5$–$C_6$ heterocycloalkyl groups include tetrahydrofuranyl, tetrahydropyranyl, piperidinyl and pyrrolidinyl groups.

Typical $C_3$–$C_{15}$-dialkylaminoalkyl groups include N,N-dimethylaminomethyl, N,N-dimethylaminoethyl, N,N-dimethylaminopropyl and N,N-dimethylaminobutyl.

With reference to Formula (XVI), a most preferred compound, wherein X, Y, R and $R^1$ are hydrogen (n is 0), is (+) and/or (−) 10,5-(iminomethano)-10,11-dihydro-5H-dibenzo[a,d]cycloheptene (IDDC) having the following Formula (XVIII):

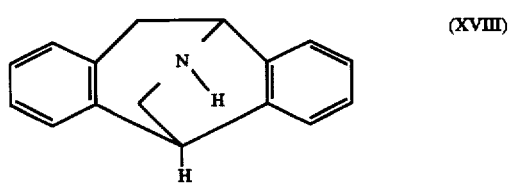

With reference to Formula (XVI), a second preferred compound wherein X, Y and R are hydrogen (n=0) and $R^1$ is $CH_3$ is (+) and/or (−) 5-methyl-10,5-(iminomethano)-10,11-dihydro-5H-dibenzo[a,d]cycloheptene (5-methyl-IDDC) having the following Formula (XIX):

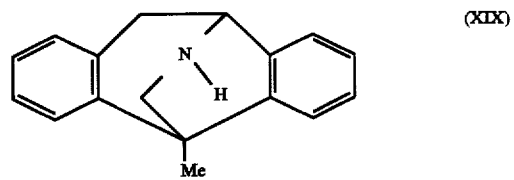

With reference to Formula (XVI), a third preferred compound wherein X, Y and $R^1$ are hydrogen (n=0) and R is $CH_3$ is (+) and/or (−) N-methyl-10,5-(iminomethano)-10,11-dihydro-5H-dibenzo[a,d]cycloheptene (N-methyl-IDDC) having the following Formula (XX):

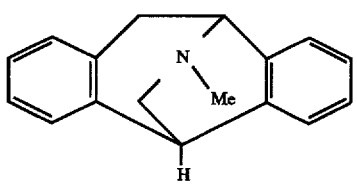

(XX)

With reference to Formula (XVI), a fourth preferred compound wherein X and Y are hydrogen and R and R¹ are CH₃ is (+) and/or (−) 5-methyl-N-methyl-10,5-(iminomethano)-10,11-dihydro-5H-dibenzo[a,d]cycloheptene (5-methyl-N-methyl-IDDC) having the following Formula (XXI):

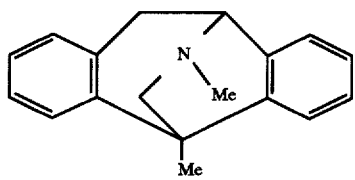

(XXI)

The compounds of the invention exhibit high binding activity with respect to the PCP receptor in mammalian nerve cells. Compounds with especially high binding activity include those represented by Formulae (XVIII)–(XXI), above.

The present invention is also directed to novel derivatives of IDDC (IDDC=(+) and/or (−) 10,5-(iminomethano)-10,11-dihydro-5H-dibenzo[a,d]cycloheptene), pharmaceutical compositions thereof, as well as the use thereof for treating or preventing neuronal loss and inhibiting NMDA receptor-ion channel related neurotoxicity. The novel IDDC derivatives which may be used in the practice of the invention include (−)-3-Chloro-5-(iminomethano)-10,11-dihydro-5H-dibenzo-[a,d]cycloheptene, (+) 3-Chloro-5-(iminomethano)-10,11-dihydro-5H-dibenzo-[a,d]cycloheptene, (−)-N-methyl-3-Chloro-5-(iminomethano)-10,11-dihydro-5H-dibenzo-[a,d ]cycloheptene, (+)-N-methyl-3-Chloro-5-(iminomethano)-10,11-dihydro-5H-dibenzo-[a,d] cycloheptene, 3-iodo-5-(iminomethano)-10,11-dihydro-5H-dibenzo-[a,d]cycloheptene, N-methyl-3-iodo-5-(iminomethano)-10,11-dihydro-5H-dibenzo-[a,d] cycloheptene, 7-Methoxy-5-(iminomethano)-10,11-dihydro-5H-dibenzo-[a,d]cycloheptene, 3-bromo-5-(iminomethano)-10,11-dihydro-5H-dibenzo-[a,d] cycloheptene, 3-chloro-7-methoxy-5-(iminomethano)-10,11-dihydro-5H-dibenzo[a,d]cycloheptene, 3-bromo-7-methoxy-5-(iminomethano)-10,11-dihydro-5H-dibenzo[a,d]cycloheptene, 7-Chloro-5-(iminomethano)-10,11-dihydro-5H-dibenzo-[a,d]cycloheptene, 3-amino-5-(iminomethano)-10,11-dihydro-5H-dibenzo[a,d]cycloheptene, 3-bromo-N-methyl-5-(iminomethano)-10,11-dihydro-5H-dibenzo[a,d]cycloheptene, 3-Bromo-7-methoxy-N-methyl-5-(iminomethano)-10,11-dihydro-5H-dibenzo[a,d] cycloheptene, (−)-3-fluoro-5-(iminomethano)-10,11-dihydro-5H-dibenzo-[a,d]cycloheptene, (+)-3-fluoro-5-(iminomethano)-10,11-dihydro-5H-dibenzo-[a,d] cycloheptene, (−)-N-methyl-3-fluoro-5-(iminomethano)-10,11-dihydro-5H-dibenzo-[a,d]cycloheptene, (+)-N-methyl-3-fluoro-5-(iminomethano)-10,11-dihydro- 5H-dibenzo-[a,d] cycloheptene, 3-methoxy-5-(iminomethano)-10,11-dihydro-5H-dibenzo-[a,d]cycloheptane, 3-nitro-5-(iminomethano)-10,11-dihydro-5H-dibenzo-[a,d]cycloheptene, 3-azido-5-(iminomethano)-10,11-dihydro-5H-dibenzo-[a,d] cycloheptene, 3-trifluoromethyl-5-(iminomethano)-10,11-dihydro-5H-dibenzo-[a,d]cycloheptene, N-methyl-3-trifluoromethyl-5-(iminomethano)-10,11-dihydro-5H-dibenzo[a,d]cycloheptene, 3,7-difluoro-5-(iminomethano)-10,11-dihydro-5H-dibenzo-[a,d]cycloheptene,3-phenyl-5-(iminomethano)-10,11-dihydro-5H-dibenzo-[a,d] cycloheptene, 3-amino-5-(iminomethano)-10,11-dihydro-5H-dibenzo-[a,d]cycloheptene, 8-hydroxy-5-(iminomethano)-10,11-dihydro-5H-dibenzo-[a,d] cycloheptene, 3-hydroxy-5-(iminomethano)-10,11-dihydro-5H-dibenzo-[a,d]cycloheptene, 8-methoxy-5-(iminomethano)-10,11-dihydro-5H-dibenzo-[a,d] cycloheptene, 3-cyano-5-(iminomethano)-10,11-dihydro-5H-dibenzo-[a,d]cycloheptene, and 3-methylthio-5-(iminomethano)-10,11-dihydro-5H-dibenzo-[a,d ]cycloheptene. Such IDDC derivatives may be racemic or optically pure, e.g. the (+) or (−) optical isomers.

Further, this invention relates to a method of ameliorating the neurotoxic effect induced by glutamate interacting with the NMDA receptor of a nerve cell, comprising the administration, to an animal, e.g., a human being, exhibiting symptoms of or susceptible to such neurotoxic effect, of a compound of the invention which has a high affinity for the PCP receptor of the nerve cell in an amount effective to block the ion channel of the NMDA receptor-ion channel complex. Such neurotoxic effects may be caused by ischemic brain insults which cause excessive release of endogenous glutamate. The pharmaceutical compositions of the invention may be administered prophylactically, for example, before a surgical procedure or other treatment which may be expected to cause reduced blood flow to the brain or spinal cord, thereby, preventing or ameliorating neurodegradation. The pharmaceutical compositions of the invention may also be administered after trauma to, for example, the head or spinal cord to prevent or ameliorate the resulting neurodegeneration which may result therefrom.

A number of disorders of the nervous system are associated with neurodegradation that may be caused by over-activation of NMDA receptors. Therefore, agents which block responses to NMDA receptor activation have therapeutic use in the treatment of neurological disorders and also in the prevention of nerve cell death resulting from hypoxia or hypoglycemia or following brain ischemia which occurs during stroke, trauma and heart attack. Antagonists of NMDA receptor-mediated responses also are useful for the treatment of such disorders as Alzheimer's disease, Huntington's chorea, amyotrophic lateral sclerosis and Down's Syndrome.

The invention also relates to a method of inhibiting NMDA receptor ion channel-related neurotoxicity comprising administering to an animal a compound of Formula (XVI) which possesses a high affinity for the PCP receptor of a nerve cell, in an amount effective to inhibit the neurotoxicity.

One of ordinary skill in the art may readily determine the activity of a particular compound represented by Formula (XVI) as a non-competitive blocker of NMDA receptor agonist by: (a) determining the binding affinity with respect to the PCP receptor by competitive displacement of tritiated thienylcyclohexylpiperidine ([³H]TCP; see Vignon et al, Brain Res. 280:194–197 (1983); Contreras et al., Neurosci Lett. 67:101–106 (1986)); (b) evaluating the ability of compounds to block the passage of ions through ion channels by measurement of electrical current through the channel (Huettner and Bean, Proc. Natl Acad. Sci. (USA) 85:1307–1311 (1988)); (c) in vitro cytotoxicity studies measuring the ability of the compound to prevent nerve cell death caused by exposure to glutamate; and/or (d) determination of in vivo neuroprotective ability using animal models.

Evaluation of the binding activity of organic compounds with respect to the PCP receptor is performed using radioligand binding assays. The compounds are tested to determine their ability to displace tritiated-TCP and tritiated-MK-801 which are used to label PCP receptors. Evaluating the competitive displacement binding data, the preferred compounds are those which exhibit a high affinity (i.e., low $IC_{50}$ value) for the PCP receptors.

Under the binding activity studies, an $IC_{50}$ value of at most about 1000 nM, preferably at most about 500 nM, indicates a high binding affinity. In the present application, the term "high affinity" is intended to mean a compound which exhibits an $IC_{50}$ value of at most about 1000 nM.

In the electrophysiological studies the compounds are evaluated with respect to their ability to block the ion channel of the NMDA receptor channel complex and thereby inhibit $Ca^{2+}$ and $Na^+$ ion flow into the nerve cell. Initially, the ion channels are opened by activating the NMDA receptor. Ion flow is determined by measuring the passage of electrical current, i.e., a use-dependent decrease in electrical current indicates blocking of the ion channel due to binding of a ligand at a site within the channel.

A use-dependent block means that as more NMDA receptor-channel complexes are activated by glutamate, blockage of the channels by the non-competitive blocking agent become more effective.

In the cytotoxicity studies, cultured mammalian neurons expressing EAA receptors are exposed in vitro to glutamate and the particular compound under investigation. The survival percentage of cells indicates the ability of the compound to protect against glutamate-induced neuronal death.

In the in vivo neurotoxicity studies, the experimental model of McDonald, D. W., et al., (In: Sigma and Phencyclidine-like Compounds as Molecular Probes in Biology, Ed. Domino, E. F., and Kamenka, J.-M., pp. 697–707 (1988), NPP Books, Ann Arbor, Mich.) may be employed. In this model, NMDA injection into one cerebral hemisphere causes injury which resembles the lesion produced by hypoxia-ischemia. The ability of compounds to limit the NMDA-induced lesion is a measure of their neuroprotective properties; since the compounds may be administered intraperitoneally, the model can also provide information about a compound's ability to cross the blood-brain barrier.

In general, the compounds having Formula (XVI) are prepared according to Scheme I shown below, for example, by heating the diaryl derivative having Formula (XXII) with bromoacetaldehyde diethylacetal in a polar aprotic solvent. Polar aprotic solvents which can be used for this purpose include N,N-dimethylformamide (DMF) and dimethylsulfoxide (DMSO). The temperature of the reaction mixture may range from 70° C. to 120° C. The product having the Formula (XXIII) is then treated with an acid such as trifluoromethanesulfonic acid or 70% perchloric acid in a solvent such as chloroform or dichloromethane at ambient temperature to give a compound having the Formula (XXIV). This compound may then be derivatized at the nitrogen atom with a suitable electrophile to give the compound represented by Formula (XVI). For example, the N-methyl derivative may be prepared by reaction of (XXIV) with formaldehyde and sodium borohydride. Alternatively, the nitrogen of Formula (XXIV) may be reacted with an alkyl halide, alkanoyl halide, or other suitable electrophile.

Where X and Y are not hydrogen, the product having Formula (XVI) may be prepared by selecting an appropriately substituted diaryl derivative (XXII) which may be prepared by electrophilic substitution on the phenyl ring(s) according to methods known to those skilled in the art.

Where Z is a carbon atom bearing a hydroxy or an alkoxy substituent, the compounds may be prepared according to U.S. Pat. Nos. 3,509,158, 3,426,015 and 3,361,767, the disclosures of which are incorporated herein by reference.

Scheme I

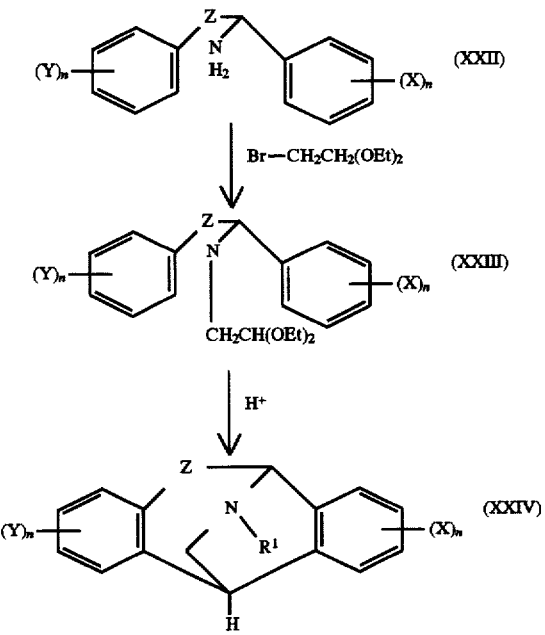

The 5-substituted derivatives of Formula (XVI) may be prepared according to Scheme II shown below, for example, by treatment of the diaryl derivative (XXII) with an alkynyl derivative (XXV) such as 3-bromo-1-propyne in an alcoholic medium containing a base such as potassium carbonate to give the substituted N-propargyl-1,2-diarylethylamine (XXVI). Where Z is a carbon atom bearing a hydroxy group, the hydroxy group may be protected by a suitable hydroxy protecting group such as benzyl and the like. Treatment of (XXVI) with an acid such as trifluoromethanesulfonic acid gives a compound having formula (XXVII). This product may be further derivatized at the nitrogen or hydroxy group (where Z is substituted by alkoxy or acyloxy) by treatment with an appropriate electrophile, as discussed above.

Scheme II

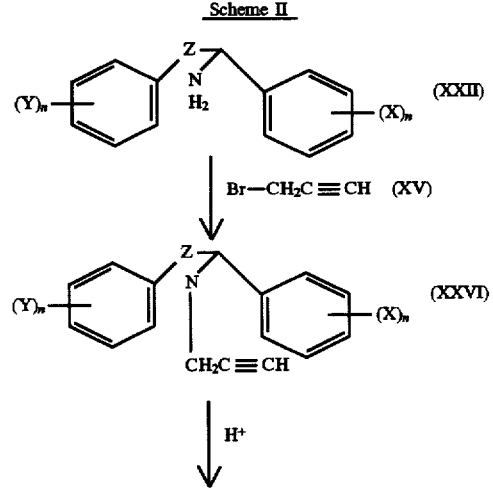

-continued
Scheme II

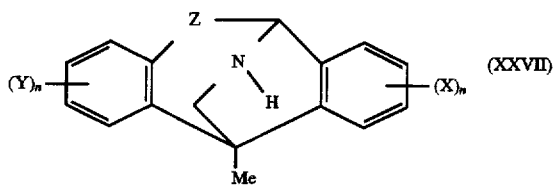
(XXVII)

Also included within the scope of the present invention are the optical isomers of the compound having Formula (XVI). The optical isomers may be separated by classical resolution techniques by, for example, formation of a salt of the amino group of Formula (XVI) with an optically active acid. A particularly preferred acid for this purpose is (+)-di-p-toluoyl-D-tartaric acid. The resulting diastereoisomeric salt may then be separated by crystallization, chromatography, or by taking advantage of the differing solubilities of the two diastereoisomeric salts. The free base may then be isolated by treatment with a base such as aqueous ammonia and extraction with an organic solvent.

Alternatively, the optical isomers may be prepared by resolution of the diaryl derivative (XXII). For example, 1,2-diphenylethylamine may be resolved by preparation of corresponding diastereoisomeric salt with an optically active acid. A particularly preferred acid for this purpose is L-(+)-tartaric acid. The diastereoisomeric salt may be separated by crystallization followed by isolation of the free base as discussed above. The optically active 1,2-diphenylethylamine may then be carried through the reaction sequence shown in Scheme I or II to give the optically active product having Formula (XVI).

The above synthesis was readily adapted to allow determination of the absolute configuration of (+)-IDDC as follows. (−)-1,2-Diphenylethylamine had already been shown (M. Nakazaki et al., *Bull Soc. Chem. Japan* 36:316 (1963)) to have the R-absolute configuration. During the synthesis of (+)-IDDC from (R)(−)-1,2-diphenylethylamine the R-configuration is retained and it becomes C-10 in the IDDC molecule. Therefore the absolute configuration of (+)-IDDC is R at C-10. Owing to the geometric constraints imposed on the molecule by the bicyclic ring structure, the absolute configuration at C-5 in (+)-IDDC must then be S. The full name of (+)-IDDC is therefore (+)-10(R),5(S)-(iminomethano)-10,11-dihydro-5H-dibenzo[a,d]cycloheptene.

Also included within the scope of the present invention are the non-toxic pharmaceutically acceptable salts of the compounds having Formula (XVI). Acid addition salts are formed by mixing a solution of a compound having Formula (XVI) with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like.

In the method of treatment or prevention of neuronal loss in ischemia, brain and spinal cord trauma, hypoxia, and hypoglycemia, as well as for the treatment of Alzheimer's disease, amyotrophic lateral sclerosis, Huntington's disease and Down's Syndrome, the pharmaceutical compositions of the invention may comprise the compound of Formula (XVI) at a unit dose level of about 0.01 to about 500 mg/kg of body weight, or an equivalent amount of the pharmaceutically acceptable salt thereof, on a regimen of 1–4 times per day. When used in a method of treating a disease in which the pathophysiology of the disorder involves NMDA receptor-ion channel related neurotoxicity, the compound having Formula (XVI) may be administered at a unit dosage level of from about 0.01 to about 500 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The pharmaceutical compositions of the invention may be administered to any animal which may experience the beneficial effects of the compounds of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, are present at a concentration of from about 0.01 to 99 percent, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions Of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Example 1

Synthesis of IDDC

A. Synthesis of N-(2,2-diethoxyethyl)-diphenylethylamine

N-(2,2-diethoxyethyl)-diphenylethylamine was prepared according to the procedure of Takayama, H., *Chem. Lett.* 865 (1978). To a stirred solution of 1,2-diphenylethylamine (3.94 g, 20.0 mmol, Aldrich Co., used as received) in N,N-dimethylformamide (DMF) (10 ml) at 80°–90° C. was added dropwise over 1 h freshly distilled bromoacetaldehyde diethylacetal (4.50 g, 22.5 mmol, Aldrich Co.). After 1 h, potassium carbonate (2.76 g, 20.0 mmol) was added. After 13 h, the brown mixture was cooled to 25° C. and then the mixture was diluted with 1N NaOH (200 ml), extracted twice with $CH_2Cl_2$ (total of 100 ml), and dried ($MgSO_4$). The solvent was evaporated and the residue was distilled to give N-(2,2-diethoxyethyl)-diphenylethylamine (5.29 g, 84%): bp 150°–160° C./0.50 mm;

$^1$H NMR ($CDCl_3$) δ1.10 (t, 3), 1.12 (t, 3), 1.70 (bs, 1), 2.50 (dd, 1), 2.5 (dd, 1) 2.58 (dd, 1) 2.91 (dd, 1), 2.98 (dd, 1), 3.39 (dt, 1), 3.44 (dt, 1), 3.54 (dt, 1), 3.86 (dd, 1), 4.53 (dd, 1), 7.16–7.40 (m, 10); $^{13}$C NMR ($CDCl_3$) δ15.5 (q), 45.5 (t), 50.0 (t), 62.0 (t), 62.2 (t), 64.9 (d), 102.0 (d), 126.5, 127.3, 128.5, 129.5 (all d), 139.0, 143.8 (all s).

B. Synthesis of IDDC and the hydrochloride salt thereof

To a stirred solution of the acetal obtained above (2.16 g, 6.90 mmol) in $CDCl_3$ (5 ml) at 25° C. was added dropwise trifluoromethanesulfonic acid (4.0 g, 36 mmol, Aldrich Co.). NMR spectroscopy indicated that the reaction was complete after 54 h. The black solution was diluted with water (50 ml), made basic with 1N NaOH (200 ml), and extracted with $CH_2Cl_2$. The extract was concentrated to dryness and the residue was purified by flash chromatography over silica gel. Elution with 10:1 ether-THF gave first a small amount of 1,2-diphenylethylamine followed by a colorless fraction which was distilled at 170° C./0.5 mm to give an oily product (1.15 g, 75%) which solidified upon standing: mp 79°–81° C. (lit.mp 74°–78° C.; Dobson, T. A., *Chem. Abstr.* 73:3816 (1970), U.S. Pat. No. 3,509,158 (1970); lit m.p. 79° C., Takai, H. et al., *Chem. Pharm. Bull.* 34:1901 (1986)); $^1$H NMR ($CDCl_3$) δ2.18 (bs, 1, NH), 3.23 (dd, 1, J=17.5 and 3.2, H-11), 3.33 (dd, 1, J=11.3 and 4.7, H-12), 3.50 (dd, 1, J=17.5 and 3.7, H-11), 3.67 (d, 1, J=11.3, H-12), 3.92 (d, 1, J=4.7, H-5), 4.33 (dd, 1 J=3.7 and 3.2, H-10), 7.04–7.38 (m, 8H-1–4; 6–9); $^{13}$C NMR ($CDCl_3$) δ41.8 (t), 47.0 (d), 50.8 (t), 55.1 (d), 125.1, 125.6, 126.1, 126.8, 126.9, 127.3, 128.1, 131.5 (all d), 135.4, 140.5, 141.6, 143.1 (all s); MS m/e 221 (40, M$^{+1}$), 220 (35), 192 (100), 191 (47).

HCl gas was bubbled into a solution of the product (700 mg) in ether (10 ml) and MeOH (10 ml) at 25°–30° C. until no more precipitate formed. The solvent was removed and the residue was dissolved in hot EtOH and than allowed to cool, giving the hydrochloride salt of IDDC (429 mg, 52%) as white crystals: mp 305°–307° C. (lit. mp.>270° C., see Dobson, T. A. et al., U.S. Pat. No. 3,509,158 (1970); *Chem. Abstr.* 73:3816 (1970)); $^1$H NMR ($CD_3OD$) δ3.31 (dd, 1), 3.54 (dd, 1), 3.78 (dd, 1), 3.85 (d, 1), 4.25 (d, 1), 5.01 (t, 1), 7.07–7.46 (m, 8); $^{13}$C NMR ($CD_3OD$) δ36.5 (t), 43.5 (d), 48.3 (t), 54.9 (d), 125.7, 126.6, 126.8, 127.7, 127.9, 128.1, 129.5, 130.9 (all d), 132.0, 132.1, 140.0, 140.3 (all s).

Example 2

Synthesis of 5-Methyl-IDDC

A. N-Propargyl-1,2-diphenylethylamine

To a stirred solution of 1,2-diphenylethylamine (930 mg, 4.20 mmol) in EtOH (30 ml) were added 3-bromo-1-propyne (700 mg, 5.30 mmol) and potassium carbonate (1.38 g, 10.0 mmol). The mixture was refluxed for 16 h and then more 3-bromo-1-propyne (100 rag) was added. The mixture was refluxed another 6 h and then it was cooled, diluted with 1N NaOH (200 ml) and extracted with $CH_2Cl_2$. The extract was dried ($MgSO_4$) and concentrated. The residue was purified by flash chromatography. Elution with 1:1 hexanes-$CH_2Cl_2$ gave first N,N-di-propargyl-1,2-diphenylethylamine (218 mg, 19%) [$^1$H NMR ($CDCl_3$) δ2.34 (t, 2), 2.83 (dd, 1), 3.53 (dd, 1), 3.63 (dd, 2), 3.71 (dd, 2), 3.85 (dd, 1), 6.89–6.92 (m, 2), 7.14–7.26 (m, 8); $^{13}$C NMR ($CDCl_3$) δ40.5 (t), 40.9 (t), 68.2 (d), 73.4 (d), 79.4 (d), 126.1, 127.6, 128.1, 128.3, 128.8, 129.7, 129.8 (all d), 138.8, 140.8 (all s)]followed by N-propargyl-1,2-diphenylethylamine. Distillation at 180° C./0.5 mm gave the pure compound (583 mg, 59%) as a colorless oil: $^1$H NMR ($CDCl_3$) δ1.69 (bs, 1), 2.20 (t, 1), 2.95 (dd, 1), 3.06 (dd, 1), 3.24 (dd, 1), 3.36 (dd, 1), 4.21 (dd, 1), 7.25–7.50 (m, 10); $^{13}$C NMR ($CDCl_3$) δ36.0 (t), 45.1 (t), 62.6 (d), 71.6 (d), 82.2 (s), 126.7, 127.6, 127.8, 128.7, 129.5 (all d), 138.6, 142.7 (all s).

B. 5-Methyl-IDDC

A solution of N-propargyl-1,2-diphenylethylamine (125 mg, 0.530 mmol) in chloroform (0.5 ml) and trifluoromethanesulfonic acid (500 mg, 3.33 mmol) was stirred for 48 h at 25° C. NMR spectral analysis of an aliquot revealed that only about a 40% conversion had taken place. Therefore, additional trifluoromethanesulfonic acid (500 mg) was added. After 24 h, the black solution was made basic with 1N NaOH (50 ml) and extracted with $CH_2Cl_2$. The solvent was evaporated and the residue was distilled to give the product (96 mg, 78%) as a colorless oil, bp 190°–200° C./0.5 mm. $^1H$ NMR ($CDCl_3$) δ1.88 (s, 3), 2.44 (s, 1), 3.09 (d, 1), 3.32 (dd, 1), 3.59 (d, 1), 3.61 (dd, 1), 4.35 (dd, 1), 7.07–7.42 (m, 8); $^{13}C$ NMR ($CDCl_3$) δ22.6 (q), 41.9 (t),55.5 (d), 58.1 (t), 62.6 (s), 122.9, 123.9, 125.0, 125.7, 126.4, 126.6, 127.3, 131.7 (all d), 136.3, 140.6, 144.3, 145.5 (all s).

Example 3

Preparation of (+)-IDDC

A. Resolution of (±)-1,2-diphenylethylamine

The general procedure of V. M. Potapov et al was adapted for the following resolution (Potapov, V. M., et al., *J. Org. Chem.* USSR 16:683 (1980)). To a stirred solution at 45° C. of 9.5013 grams (63.2 mmoles) of L-(+)-tartaric acid (Mallinkrodt, used as received) in 400 mL of water was added dropwise, 24.7673 grams (125.5 mmoles) of (±)-1,2-diphenylethylamine (Aldrich, used as received). A white precipitate formed immediately. After stirring for 2.5 hours at 250° C. the precipitate was collected and partially air dried to yield 94 grams of white solid. These 94 grams were dissolved in 300 mL of boiling water then filtered while hot to give a clear, colorless solution. Crystallization commenced from this solution within 20 min. The collected crystals amounted to 31.6 grams after partial air drying. Subsequently, five more recrystallizations were performed on this material using proportional amounts of boiling water to give 905.2 mg of the partially resolved diastereoisomeric salt of (+)-L-tartaric acid and (+)-1(R),2-diphenylethylamine as white microcrystals; mp 222.5°–223.5° C. dec, $[\alpha]_D^{19}$=–51.3° C. =0.92, $H_2O$. Nakazaki et al., *Bull Chem. Soc. Jpn.* 36:161 (1963) report the following physical constants: (+)-tartrate of (–)-1(R),2-diphenylethylamine MP 229°–230° C., $[\alpha]_D^{19}$=–55.3°, C=0.92, $H_2O$; (–)-1(R),2-diphenylethylamine $[\alpha]_D^{19}$=–51.2°, C=3.7, EtOH. The mother liquors from the last four recrystallizations were combined. The aqueous solution was concentrated, made basic by the addition of solid NaOH and extracted with three portions of $CH_2Cl_2$. The combined organic layers after drying ($K_2CO_3$) and removal of the solvent in vacuo yielded 2.5397 grams of partially resolved (–)-1(R),2-diphenylethylamine; $[\alpha]_D^{19}$=–44.0° C., C=3.7, EtOH (Nakazaki, M., et al.; supra). The amine (2.5055 grams, 12.7 mmoles) was added dropwise to a stirred solution at 45° of 1.8116 grams (12.1 mmoles) of L-(+)-tartaric acid (Mallinkrodt, used as received) in 40 mL of water. The resulting white precipitate was collected after the mixture had stirred at ambient temperature for 12 hours. The collected solid was recrystallized three times from boiling $H_2O$ to yield 815.2 mg of the diastereoisomeric salt of (+)-L-tartaric acid and (–)-1(R),2-diphenylethylamine as white microcrystals; mp 224°–225° C. dec, $[\alpha]_D^{19}$=–54.8°, C=0.92, $H_2O$. Nakazaki et al., supra. The salt (806.6 mg) was dissolved in 50 mL of 1N NaOH and 25 mL of $CH_2Cl_2$. The layers were separated and the aqueous portion was extracted with 2×25 mL of $CH_2Cl_2$. The combined organic layers were washed with 15 ml of 1N NaOH, dried ($K_2CO_3$), and the solvent removed at reduced pressure to give 449.1 mg of (–)-1(R),2-diphenylethylamine as a colorless liquid; $[\alpha]_D^{19}$=–50.1°, C=3.7, EtOH.

B. Preparation of N-(1(R),2-diphenylethyl) aminoacetaldehyde diethyl acetal The general procedure of Suzuki, T., et al., *Chem. Pharm. Bull* 34:1988 (1986), was adapted for the following alkylation. To a stirred mixture at 90° C. of 249.5 mg (1.3 mmoles) of (–)-1(R),2-diphenylethylamine and 193.6 mg (1.4 mmoles) of anhydrous potassium carbonate (Baker, used as received) in 2.5 ml of N,N-dimethylformamide (Baker, used as received) was added dropwise, over two hours, a solution of 284.1 mg (1.4 mmoles) of bromoacetaldehyde diethylacetal (Aldrich, distilled, bp 83° C./40mm). The resulting mixture was heated (95°–105° C.) with stirring. After 16 hours the reaction mixture was cooled to 10° C., 50 mL of 1N NaOH was added followed by 25 mL of $CH_2Cl_2$. The layers were separated and the aqueous layer was extracted with 2×15 mL of $CH_2Cl_2$. The combined organic layers were washed with 10 mL of 1N NaOH, dried ($K_2CO_3$) and the solvent evaporated at reduced pressure to give 346.1 mg of brown oil. The oil was distilled (180°–190° C., 0.05 mm/Hg) using a Kugelrohr apparatus to give 315.5 mg of light yellow off. The yellow off (304.2 mg) was chromatographed (10 g silica gel) using 25 mL $ET_2O$ followed by 40 mL 3:1 $Et_2O$/THF then 40 mL 2:1 $Et_2O$/THF as eluent. The fractions containing the less polar material (Rf 0.56) were combined and the solvent removed at reduced pressure yielding 283.3 mg of N-(1(R),2-diphenylethyl) aminoacetaldehyde diethyl acetal as a clear, light yellow liquid (71% yield).

$^1H$ NMR ($CDCl_3$): δ1.09 and 1.11 (t, 6H, J=6.9, —$CH_3$), 1.76 (bs, $^1H$, NH), 2.51 (dd, 1H, J=12.0 and 6.3, —$CH_2$—N), 2.57 (dd, 1H, J=12.0 and 5.0, —$CH_2$—N), 2.91 (dd, 1H, J=13.2 and 8.5, $CH_2$-Phenyl), 2.98 (dd, 1H, J=13.2 and 5.9, —$CH_2$-Phenyl), 3.37 and 3.43 (dt, 2H, J=9.3 and 7.2, —$CH_2$—O), 3.53 and 3.57 (dt, 2H, J=9.3 and 6.9, —$CH_2$—O), 3.86 (dd, $^1H$, J=8.5 and 5.9, —CH—N), 4.53 (dd, 1H, J=6.3 and 5.0, —CH—O), 7.16 –7.34 (m, 10H, Phenyl).

C. Preparation of (+)-10,5-(Iminomethano)-10,11-dihydro-5H-dibenzo[a,d]cycloheptene (IDDC)

The general procedure of T. Suzuki et al., supra, was adapted for the following cyclization. To 6 ml of perchloric acid (70% aqueous) at 24° C. was added dropwise with stirring over 5 min. 280 mg (8.9 mmoles) of N-(1(R),2-diphenylethyl)aminoacetaldehyde diethyl acetal. During the addition a brown oil separated. The mixture was stirred for 16 hours at ambient temperature then poured onto 50 mL of 2N NaOH and extracted with 3×15 mL of $CH_2Cl_2$. The combined organic layers were washed with 15 mL of 1N NaOH, dried ($K_2CO_3$) and the solvent removed at reduced pressure to give 225.4 mg of brown oil. A TLC (THF) showed two spots with Rf values of 0.67 and 0.23. The oil (225 mg) was submitted to flash chromatography (8 grams silica gel) eluting with 25 mL of $ET_2O$, 40 mL 3:1 $ET_2O$/THF, 25 mL 2:1 $ET_2O$/THF, 25 mL 1:1 $Et_2O$/THF, and 25 mL THF. The fractions containing the more polar material (Rf 0.22) were combined and the solvent evaporated in vacuo to give 172.1 mg of brown oil. This oil was double distilled (175°–185° C., 0.05 mm/Hg) using a Kugelrohr apparatus to give 153.4 mg of (+)-IDDC as a clear light yellow oil that solidified on standing (mp 79°–85° C., $[\alpha]_D^{25}$=+161.5°, C=1, EtOH) (78% yield). $^1H$ NMR ($CDCl_3$): δ2.10 (bs, $^1H$, —NH), 3.23 (dd, 1H, J=17.5 and 3.2, H-11), 3.33 (dd, 1H, J=11.1 and 4.6, H-12), 3.51 (dd, 1H, J=17.5 and 3.7, H-11), 3.67 (d, 1H, J=11.1, H-12), 3.93 (d, 1H, J=4.2, H-5), 4.34 (t, 1H, J=3.6, H-10), 7.05–7.30 (m, 8H, H-1,2,3,4,6,7,8,9). $^{13}$C NMR (CDCl$_3$): δ41.7 (t, C-11), 46.9 (d, C-5), 50.8 (t, C-12), 55.1 (d, C-10), 125.0, 125.6, 126.0, 126.8, 126.9, 127.3, 128.0, 131.5 (d, C-1,2,3,4,6,7, 8,9), 135.4, 140.4, 141.6, 143.0 (s, C-4a,5a,9a,11a).

D. Preparation of the Maleate Salt of (+)-IDDC

To a stirred solution at 43° C. of 50.6 mg (0.23 mmoles) of (+)-IDDC in 1.0 ml of EtOH was added a solution of 26.4 mg (0.23 mmoles) of maleic acid (Aldrich, used as received) in 0.3 ml of EtOH. Crystallization begins from the resulting solution in approximately 10 minutes. This mixture was then stirred at ambient temperature. After 14 hours, the white crystals were collected and then recrystallized from 0.4 ml of hot EtOH to give 31.1 mg of the maleate salt of (+)-IDDC (mp 168°–168.5° C. dec). From the mother liquors were isolated, after recrystallization, two subsequent portions of the maleate salt of 10.2 mg (mp 167°–167.5° C. dec) and 13.8 mg (mp 164°–165.6° C. dec).

Example 4

Preparation of Optically Active N-Methyl-IDDC

To a stirred solution of (+)-IDDC (9.3 mg, 0.04 mol; $[α]_D$=+116.3°, EtOH, c=1) in acetonitrile (0.4 ml) and 37% aqueous formaldehyde (0.61 mmol) at 25° C. was added sodium cyanoborohydride (5.1 mg, 0.08 mmol). The resulting mixture was stirred for 15 min. and then one drop of glacial acetic acid was added to lower the pH to 7 (checked by wet pH paper). The mixture was stirred for 20 h and the solvent was removed in vacuo. The residue was treated with 2N sodium hydroxide (4 ml) and ether (4 ml). The layers were separated and the aqueous layer was extracted with ether. The combined organic layers were dried (K$_2$CO$_3$), filtered, and evaporated to give a clear oil (11 mg) which was purified by preparative TLC on silica gel. Elution with ethanol gave two bands, R$_f$=0.41 and 0.83. The baud at 0.41 was removed and extracted with acetone. The solution was dried (K$_2$CO$_3$) and evaporated to give optically active N-methyl IDDC (10.6 mg, 84%) as an off-white oil;

$^1$H NMR (CDCl$_3$) δ2.50 (s, 3, N—Me), 2.92 (dd, 1, J=10.5 and 4.8, H-12), 3.00 (dd, 1, J=17.7 and 3.3, H-11), 3.58 (dd, 1, J=10.5 and 1.1, H-12), 3.62 (dd, 1, J=17.7 and 3.9, H-11), 3.83 (dd, 1, J=4.7 and 1.1, H-5), 3.94 (dd, 1, J=3.9 and 3.0, H-10). $^{13}$C NMR (CDCl$_3$) δ38.61 (t), 45.2 (q), 47.0 (d), 59.8 (t), 62.7 (d), 125.1, 125.9, 126.0, 126.7, 127.3, 127.8, 131.3 (all d), 135.2, 138.6, 141.4, 142.5 (all s).

Example 5

The PCP Receptor Binding Properties of the IDDC Optical Isomers

The PCP receptor binding properties of various compounds of the invention against $^3$H-5-methyl-10,11-dihydro-5H-dibenzo[a,d]cycloheptene-5,10-imine ($^3$H-MK-801) were determined. The results appear in Table 1, below.

TABLE 1

| Compound | IC$_{50}$[+sem(n)] $^3$H-MK-801 (nanomolar) |
|---|---|
| (±)-IDDC | 41 ± 6(5) |
| (+)-IDDC | 40 ± 5(4) |
| (+) N-Methyl-IDDC | 800 ± 9(3) |
| (±) 5-Methyl-IDDC | 125(1) |

Example 6

Electrophysiological Assays (+)-IDDC was tested for ill ability to achieve use-dependent blockage of NMDA-induced (+glycine) responses on rat hippocampal neurons maintained in cell culture. This compound produced a result very similar to the use dependent blocking action exhibited by MK-801.

Hippocampal neurons were obtained from the CA1 region of the hippocampus from 1–3 day-old-newborn rats (Long-Evans). Small blocks of tissue (>1mm$^3$) were incubated in papain (20 units ml$^{-1}$; Worthington-Cooper) for 30 minutes. The tissue was dissociated into a single cell suspension by trituration with a fire-polished Pasteur pipette in complete growth medium (Earle's MEM, 20 mM glucose, 50 units/ml penicillin/streptomycin, 5% heat-inactivated fetal calf serum, Serum Extender from Collaborative Research) containing 2.5 mg/ml bovine serum albumin and 2.5 mg/ml trypsin inhibitor (Sigma). The cells were plated onto glass coverslips coated with collagen/poly-D-lysine. Cultures were fed every 3 days by replacing haft the volume of medium. Arabinosylcytosine (5×10$^{-6}$M) was added to the cultures for 1 or 2 days during the first week after plating to suppress the proliferation of non-neuronal cells.

All electrophysiology experiments were performed with the whole-cell mode of patch clamp recording [Hamill, O. D., Marty, A., Neher, E., Sakman, B., and Sigworth, F. J., Pflugers Arch. 391:85–100 (1981)] from neurons grown for 1–3 weeks in culture. Agonists and agonist/antagonist combinations were applied by a U-tube mol (Fenwick et al, J. Physiol. 331:577–597 (1982)) to neurons in whole-cell experiments. The external solution contained (in mM) NaCl 140, KCl 3.5, CaCl$_2$ 1, glucose 5, picrotoxinin 0.02, tetrodotoxin (TTX) 5×10$^{-4}$, and N-2-hydroxyethyl-piperazine-N'-2-ethanesulfonic acid (HEPES) 10. The pH of this solution was adjusted to 7.4 with NaOH. The internal (patch electrode) solution contained (mM) Cs-methanesulfonate 120, CsCl 10, ethyleneglycol-bis-(β-aminoethylether)-N,N, N',N'-tetraacetic acid (EGTA) 10, HEPES 10 (pH adjusted to 7.0 with CsOH). Membrane current was filtered at 4000 Hz (−3dB; 8-pole Bessel) and recorded on magnetic tape for later analysis. Experiments were performed at room temperature (20°–25° C.). [Sources of chemicals: N-methyl-D-aspartate, Cambridge Research Biochemicals; pirotoxinin, Sigma Chemical Company; salts for recording solutions, Aldrich (Gold Label) or Alfa (Puratronic). [$^3$H]Kainate and [3H]CPP and [$^3$H]AMPA were purchased from Dupont/NEN (Boston, Mass.)].

Three second applications of 50 uM NMDA in the presence of 1 uM glycine resulted in inward whole-cell currents of 100–1000 pA at a holding potential of −60 mV. Repetitive applications (every 30 s) to the same cell produced currents which varied less than 5% over a period of at least 30 minutes. When MK-801 (10 uM) was applied in conjunction with NMDA, the inward current became progressively smaller with serial applications. Recovery from this inhibition required repeated applications of NMDA alone and was speeded by holding the membrane potential at positive voltages.

Identical to MK-801, (+) N-methyl IDDC (10 uM) inhibited the NMDA current in a use-dependent and voltage-dependent manner. Serial applications evoked progressively smaller currents. Inhibition by (+) N-methyl IDDC was reversed only with prolonged or repeated application of NMDA. The rate of recovery from blockade by (+) N-methyl IDDC was somewhat more rapid than the rate of recovery of responses following MK-801. This observation is consistent with the observation that (+) N-methyl IDDC has a lower affinity than MK-801 for the PCP receptor.

Example 7

In Vitro Neurotoxicity Assay

Dissociated rat hippocampal cultures were prepared using a modification of the method of Huettner and Baughman

[Huettner, J. E. and Baugham, R. W., *J. Neurosci.* 6:3044–3060 (1986)]. The cortices were removed from 1–3 day post-natal rats (Sprague-Dawley) that had been anesthetized with chloral hydrate, and the hippocampi were dissected out and placed in Cl⁻ free dissociation medium supplemented with 1 mM kynurenic acid and 10 mM $MgSO_4$ (Choi, D. W., *J. Neurosci.* 7:369–379 (1987)). The hippocampi were washed in the dissociation medium, then incubated for 2×20 minutes at 37° C. in dissociation medium containing 10 units/ml of Papain (Worthington). After the enzyme treatment, the tissue was incubated for three 5-minute periods at 37° C. with 10 mg/ml trypsin inhibitor (Sigma type II-0).

The cells were dissociated by trituration in growth medium and plated as 0.15 ml droplets of cell suspension onto the center of 35 mm Primaria (Falcon) dishes that had been stamped with a labeled 26×26 grid of approximately 0.64 cm² total area using a Mecanex BB form (WPI, New Haven, Conn.) and coated with poly-D-lysine and laminin (Collaborative Research). The cell density was between 2.5 and $4.0 \times 10^5$ cells per dish. The growth medium was Eagles minimum essential media (MEM, Earle's salts) supplemented with 5% fetal bovine serum (CCL), 5% defined supplemented calf serum (HyClone), 50 mM glucose, 50 units/ml penicillin/streptomycin and MITO+serum extender (Collaborative Research). The cells were maintained at 37° C. in a humidified 4.5% $CO_2$ atmosphere. Cells were left for 12–14 hours to attach to the plate surface, then 1.5 mls of growth medium was added to each dish, 1 ml removed and replaced with a further 1 ml of fresh medium. This process removed most of the cell debris and unattached cells. The area of cell attachment and proliferation did not significantly extend beyond the treated central area. After 2–4 days in culture, non-neuronal cell division was arrested by a 2–3 day exposure to 5 uM cytosine arabinoside.

The cells were maintained in a medium that was similar to the growth medium but without the fetal bovine serum. The medium was changed on a weekly schedule, replacing two-thirds the volume with fresh medium. The only glutamate present in the media was that contained in the calf serum which gave a final concentration of 12 uM.

Before treatment, sister cultures were examined under phase-contrast microscopy to ensure that the cultures were of a similar density. Exposure to glutamate was carried out at 32°–34° C. in a HEPES-buffered "control salt solution" (CSS) similar to that reported in Choi, D. W., Maulicci-Gedde, M. and Viriegstein, A. R., *J. Neurosci.* 7:257–268 (1987), but with 10 mM HEPES substituted for Tris-HCl and buffered for pH 7.4 at 34° C. The cultures were washed twice with CSS and then incubated for 5 minutes in CSS containing 1 uM glycine and the compound to be tested (the controls had 1 uM glycine only). Glycine was included since it has been shown to potentiate the effects of glutamate at the NMDA site [Johnson, J. W. and Ascher, P., *Nature* 325:529–530 (1987)] and the preincubation with the test drugs enhances the neuroprotection activity (Finkbeiner, S. C., et al., *Proc. Natl. Acad. Sci. USA* 85:4071–4074 (1988)). CSS containing 1 uM glycine plus drug and a known concentration of glutamate (0–1000 uM) were added by triple exchange and the cultures were incubated for 5 minutes. The cultures were washed four times with CSS and then with medium before being placed in the incubator overnight. Cultures were removed from the incubator the next day, washed twice with CSS and treated for 5 minutes with 0.4% Trypan Blue, a dye that is only taken up by dead and dying cells. The cultures were washed three times and the surviving cells counted in the grid area using phase contrast microscopy. Cell survival was normalized as a percentage of the highest cell count, and the results plotted against glutamate concentration. Cultures not exposed to glutamate generally had between 4500 and 5500 surviving cells in the grid area.

(±)-IDDC was tested for its neuroprotective properties against a range of glutamate concentrations. FIG. 1 depicts a graph showing the in vitro neuroprotective effect of (±)-IDDC, (+)-IDDC, N-methyl IDDC and a control sample on rat hippocampal cells treated with various concentrations of glutamate. As illustrated in FIG. 1, cultures tested with 5 uM (±)-IDDC, 5 uM (+)-IDDC and 10 uM N-methyl IDDC exhibited enhanced cell survival when compared to control values.

Example 8

In Vivo Neurotoxicity Assay

Figure 2:
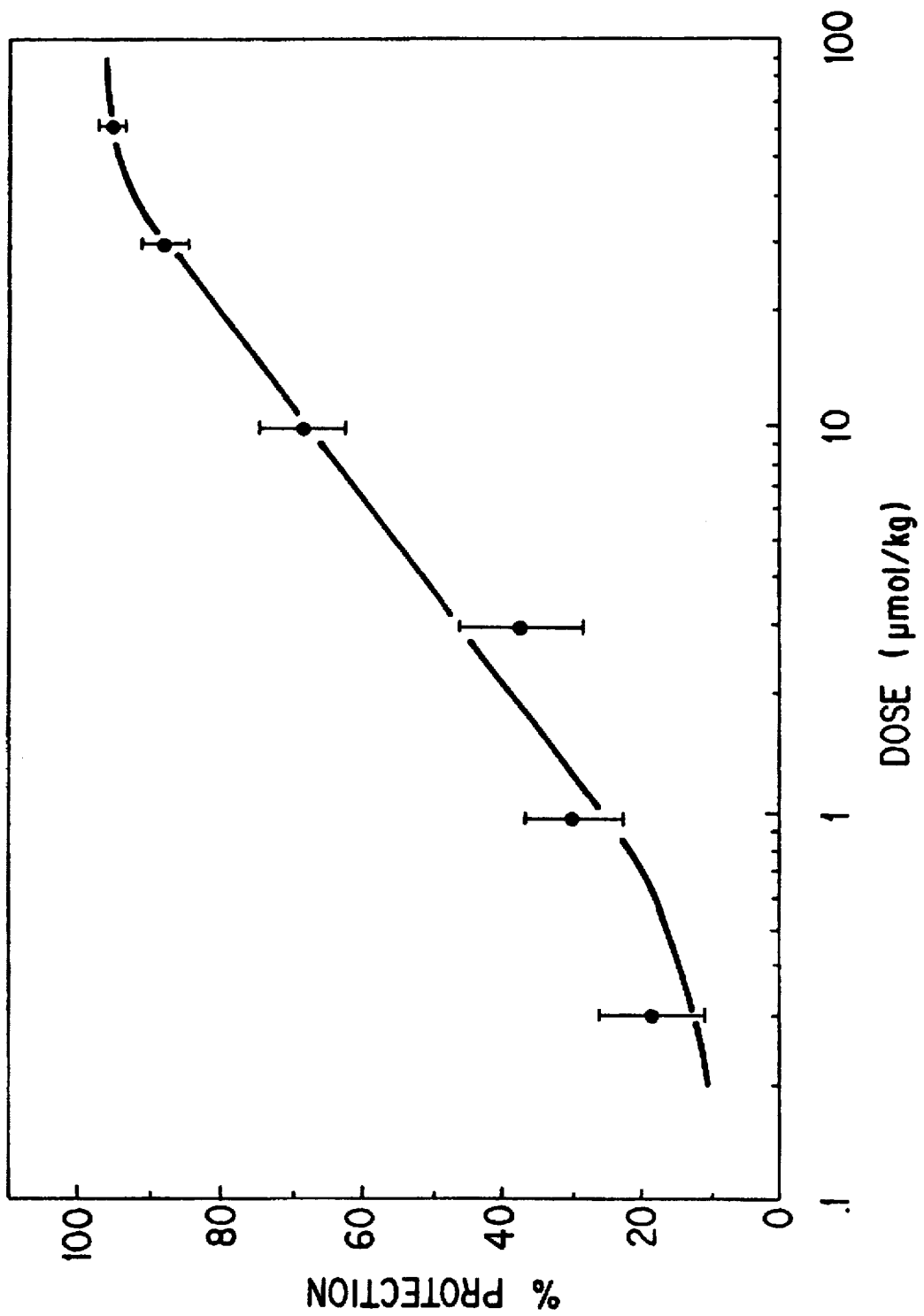
FIG. 2 depicts a graph showing the in vivo neurotoxicity protective effect of (+)-IDDC at various dosage levels.

The experimental model of McDonald, J. W., et al., supra, was employed with the single alteration in protocol of an intraperitoneal injection of the test compound 15 minutes following, rather than preceding, the cerebral NMDA injection. As shown in FIG. 2, (+)-IDDC was found, in dosages ranging from about 0.30 to 60 µMol/kg of body weight, to protect against the lesions caused by NMDA injection.

These observations on the in vitro and in vivo neuroprotective properties of IDDC are consistent with its affinity for the PCP binding site in brain and the inhibition of the NMDA current described above.

Example 9

The preparation of Aryl-substituted IDDC derivatives

The following is an experimental description of syntheses of some racemic substituted IDDC's and one optically active IDDC derivative. The synthesis for each substituted IDDC began with a Friedel-Crafts reaction of an appropriate phenylacetyl chloride with an appropriate aromatic substrate. The resulting desoxybenzoin was then converted to its methyl oxime ether using the method of Sing (Sing, P. J., *Org. Chem.* 44:843 (1979)). The syn-and anti-isomers were usually not separated, but reacted together with borane-tetrahydrofuran complex to give the corresponding amines, according to the method of Feuer and Braunstein. (Feuer et al, *J. Org. Chem.* 34:1817 (1969)). The resulting amines were alkylated with bromoacetaldehyde diethylacetal in DMF. The resulting acetals were cyclized to the corresponding IDDC's using neat perchloric or sulfuric acid, according to the method of Suzuki et al. (Suzuki et al, *H. Chem. Pharm. Bull.* 34:1888 (1986)). The N-methyl derivative of 3-bromo-IDDC was prepared. Maleate salts were prepared from 3-chloro-and 3-bromo-IDDC and maleic acid. See Scheme II for the synthetic outline and compound numerals, which are referred to throughout the Experimental section, and numbering for IDDC.

Scheme III

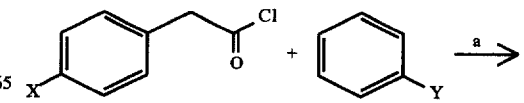

23
-continued
Scheme III

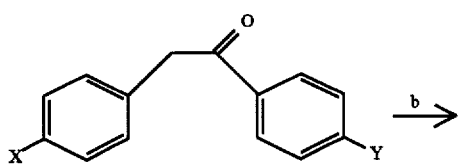

| | X = H, | Y = OMe | 1 |
|---|---|---|---|
| | Cl, | H | 2 |
| | Br, | H | 3 |
| | H, | Cl | 4 |
| | OMe, | H | 5 |

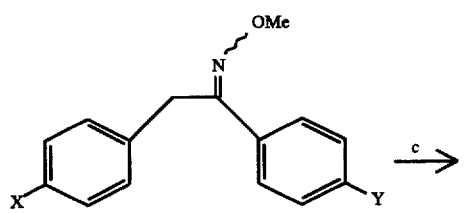

| | X = H, | Y = OMe | 6 |
|---|---|---|---|
| | Cl, | H | 7 |
| | Br, | H | 8 |
| | H, | Cl | 9 |
| | OMe, | H | 10 |

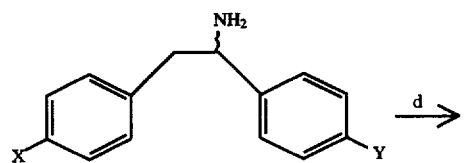

| | X = H, | Y = OMe | 11 |
|---|---|---|---|
| | Cl, | H | 12 |
| | Br, | H | 13 |
| | H, | Cl | 14 |
| | OMe, | H | 15 |

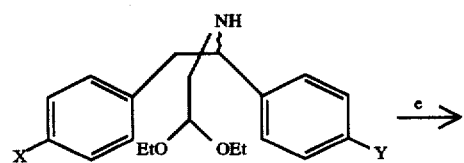

| | X = H, | Y = OMe | 16 |
|---|---|---|---|
| | Cl, | H | 17 |
| | Br, | H | 18 |
| | H, | Cl | 19 |
| | OMe, | H | 20 |

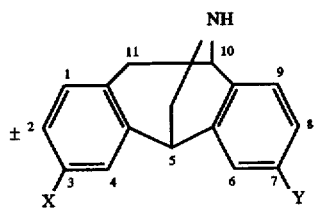

| | X = H, | Y = OMe | 21 |
|---|---|---|---|
| | Cl, | H | 22 |
| | Br, | H | 23 |
| | H, | Cl | 24 |
| | OMe, | H | 25 | a AlCl$_3$;  b CH$_3$ONH$_2$.HCl, pyridine;  c BH$_3$THF;
d BrCH$_2$CH(OEt)$_2$, K$_2$CO$_3$, DMF;  e HClO$_4$ or H$_2$SO$_4$

24

General. All reactions were carried out in glassware that had been oven dried. Except where noted, solvents were reagent grade and used as received. NMR spectra were obtained on a General Electric QE 300 instrument, and the chemical shifts are reported in delta units using residual solvent proton signals as the reference. Infrared spectra were obtained on a Nicolet 5DXB FT-IR spectrometer as 5% solutions in the indicated solvent; absorptions are classified as strong (s), medium (m), or weak (w). "Flash" chromatography was performed under positive air pressure with Davisil silica gel (grade 643, 200–425 mesh, 150 angstroms) as the stationary phase. Analytical thin layer chromatography was performed on aluminum-backed silica gel 60 $F_{254}$ plates with a fluorescent indicator, and visualization was effected with an ultraviolet lamp. All products were chromatographically homogeneous. Mass spectroscopy was carried out in the electron ionization mode.

A. Synthesis of (±) 7-Methoxy-IDDC 1-(4-Methoxyphenyl)-2-phenyl-1-ethanone (1). To a suspension of aluminum chloride (1.47 g, 11.0 mmol) in 40 ml methylene chloride (40 ml) under nitrogen was added anisole (1.30 g, 12.0 mmol, dried over molecular sieves). To the resulting light red solution was added phenylacetyl chloride (1.70 g, 11.0 mmol, prepared in 69% yield from phenylacetic acid and phosphorous trichloride) as a solution in 15 ml methylene chloride over a period of 30 minutes. The resulting light orange solution was refluxed for four hours, and after cooling poured into 100 ml ice water. The layers were separated and the organic phase washed with water (1×30 ml), 10% NaOH (1×30 ml), water (1×30 ml), and brine (1×30 ml), and dried over sodium sulfate. Concentration in vacuo afforded a white crystalline solid, which was purified by column chromatography on neutral alumina (20 g, activity I) using 3:1 benzene/ethyl acetate as eluant to afford the ketone as 2.34 g of a white crystalline solid, a portion of which was recrystallized from light petroleum ether (94% yield): m.p. 70.5°–72.0° C. (lit. m.p. 77° C.; Schneider, M. R. et at, *J. Med. Chem.* 25:1070 (1982)); R$_f$ 0.41 (benzene/ethyl acetate 9:1); IR (CDCl$_3$) 3068 (w), 3031 (w), 2970 (w), 2940 (w), 2844 (w), 1675 (s), 1602 (s), 1578 (m), 1512 (m), 1324 (m), 1263 (s), 1173 (s), 1033 (m); $^1$H NMR (CDCl$_3$) 8.03 (d, J=8.8 Hz, 2H), 7.3 (m, 5H), 6.95 (d, J=8.8 Hz, 2H), 4.26 (s, 2H), 3.88 (s, 3H).

1-(4-Methoxyphenyl)-2-phenyl-1-ethanone-O-methyl oxime (6). To a solution of 1-(4-methoxyphenyl)-2-phenyl-1-ethanone (1, 1.200 g, 5.30 mmol) in pyridine (17.0 ml, dried over molecular sieves) under nitrogen was added methoxylamine hydrochloride (0.664 g, 7.96 mmol). The resulting colorless suspension was stirred at room temperature overnight. The pyridine was removed in vacuo with heating, and the residual solids were stirred with ether (75 ml) and filtered. The filtrate was concentrated in vacuo to afford a pure mixture of the two geometric isomers as 1.311 g of a colorless, cloudy syrup (96% yield): R$_f$ 0.46, 0.32 (benzene); IR (CDCl$_3$) 3065 (w), 3005 (w), 2963 (w), 2939 (m), 2902 (w), 2822 (w), 1608 (m), 1514 (m), 1495 (m), 1465 (m), 1454 (m), 1439 (m), 1253 (s), 1179 (m), 1049 (s), 1033 (m); low resolution mass spec. 255 (M$^+$, 100), 223 (34), 208 (20), 133 (23), 91 (56).

A 210 mg sample of the isomer mixture was subjected to flash chromatography on 25 g silica gel using benzene as eluant. The less polar isomer was isolated pure as 120 mg of a clear, pale yellow syrup: $^1$H NMR (CDCl$_3$) 7.67 (d, J=8.8 Hz, 2H), 7.3 (m, 5H), 6.90 (d, J=8.8 Hz, 2H), 4.19 (s, 2H), 4.08 (s, 3H), 3.82 (s, 3H). The more polar isomer was isolated as 66 mg of a cloudy, pale yellow syrup: $^1$H NMR (CDCl$_3$) 7.38 (d, J=8.8 Hz, 2H), 7.25 (m, 5H), 6.86 (d, J=8.8

Hz, 2H), 3.96 (s, 3H), 3.88 (s, 2H), 3.80 (s, 3H). 1-Amino-1-(4-methoxyphenyl)-2-phenylethane (1H). To a solution of a mixture of syn- and anti-oxime isomers 2, (1.31 g, 5.13 mmol) in THF (50 ml, freshly distilled from sodium/benzophenone ketyl) was added borane-tetrahydrofuran complex (1.0M in THF, 25.6 ml, 25.6 mmol) via syringe at room temperature under nitrogen. The resulting clear colorless solution was refluxed for 3 ¼ hours, and cooled in an ice water bath. Water (40 ml) was carefully added, followed by 20% NaOH (40 ml). The resulting bi-phasic solution was refluxed with vigorous magnetic stirring overnight, and allowed to cool to room temperature. Hexanes (50 ml) were added, and the layers separated. The aqueous portion was extracted with hexanes (1×50 ml). The combined organic portions were dried over potassium carbonate and concentrated in vacuo to a cloudy colorless syrup, which was purified by column chromatography on neutral alumina (activity I, 35 g) using CHCl$_3$/ethyl acetate (1:1) and then pure CHCl$_3$ as eluant to give the amine as 1.024 g of a clear, colorless syrup (88% yield): R$_f$ 0.45 (4% ET$_2$NH in CHCl$_3$); IR(CDCl$_3$) 3155 (m), 3033 (w), 2926 (m), 2835 (w), 1819 (w), 1794 (w), 1611 (m), 1514 (s), 1464 (m), 1377 (m), 1250 (s), 1179 (m); $^1$H NMR δ7.35–7.17 (m, 7H), 6.90 (d, J=8.4 Hz, 2H), 4.18 (dd, J=8.6, 5.1 Hz, 1H), 3.83 (s, 3H), 3.01 (dd, J=13.2, 4.9 Hz, 1H), 2.83 (dd, J=13.2, 8.8 Hz, 1H), 1.46 (s, 2H); low resolution mass spec. 227 (M$^+$, 2), 224 (6), 211 (19), 126 (100), 121 (16), 109 (52), 91 (47).

1-(N-ethyl-(2,2-ethoxy))-amino-1-(4-methoxy-phenyl)-2-phenyl ethane (16). To a solution of the amine 11 (997 mg, 4.39 mmol) in 40 ml DMF (dried over molecular sieves) under nitrogen was added potassium carbonate (2.43 g, 17.6 mmol) and bromoacetaldehyde diethylacetal (2.16 g, 11.0 mmol, distilled) at room temperature. The resulting clear colorless suspension was heated at 100° C. for 19 hours. After cooling to room temperature, 10% NaOH (150 ml) was added. The resulting pale yellow cloudy mixture was extracted with methylene chloride (3×50 ml). The combined organic extracts were washed with water (2×50 ml) and brine (1×50 ml), and dried over potassium carbonate. Concentration in vacuo with heating afforded a red-yellow syrup, which was purified by flash chromatography on 35 g silica gel using 3:1 hexanes/ethyl acetate as eluant. The acetal 16 was obtained as 965 of a pale yellow syrup (63% yield): R$_f$ 0.30 (hexanes/ethyl acetate 2:1); IR (CDCl$_3$) 3328 (w), 3062 (w), 3031 (w), 2977 (m), 2934 (m), 2910 (m), 2838 (m), 1614 (m), 1584 (w), 1512 (s), 1457 (m), 1245 (s), 1173 (m), 1130 (s), 1057 (s); $^1$H NMR (CDCl$_3$) δ7.31–7.14 (m, 7H), 6.87 (d, J=8.6 Hz, 2H), 4.52 (t, J=5.6 Hz, 1H), 3.82 (s, 3H), 3.8 (m, 1H), 3.65–3.34 (m, 4H), 2.92 (m, 2H), 2.52 (m, 2H), 1.68 (s, 1H), 1.10 (q, J=7.2 Hz, 6H); low resolution mass spec. 344 (M$^+$+1, 8), 252 (100), 211 (50), 206 (61), 91 (23).

7-Methoxy-IDDC (21). A 5 ml round bottom flask was charged with the acetal 16 (310 mg, 0.903 mmol) under nitrogen. Perchloric acid (69%, 1.59 ml, 18.1 mmol) was added by syringe. The resulting red-yellow syrup was stirred at room temperature for 49 hours, and quenched with ice and 10% NaOH (pH>10). Extraction with methylene chloride (3×10 ml) afforded, after combination of the extracts, an organic solution that was washed with brine (1×15 ml) and dried over sodium sulfate. Concentration in vacuo afforded a dark golden syrup that was purified by flash chromatography on 12 g silica gel using an elution gradient of ethyl acetate to 15% methanol/ethyl acetate (the methanol contained 1% concentrated ammonium hydroxide). The product was isolated as 110 mg of a clear, colorless syrup (48% yield): R$_f$ 0.10 (ethyl acetate/methanol 4:1): IR (CDCl$_3$) 3352 (w), 3063 (w), 3019 (w), 2916 (m), 2831 (w), 1490 (s), 1450 (m), 1283 (m), 1249 (s), 1134 (m); $^1$H NMR (CDCl$_3$) δ7.33–7.01 (m, 5H), 6.80 (d, J=2.4 Hz, 1H), 6.76 (d, J=2.7 Hz), 6.73 (d, J=2.7 Hz, 1H over 6.76–6.73), 4.32 (t, J=3.6 Hz, 1H), 3.87 (d, J=4.1 Hz, 1H), 3.79 (s, 3H), 3.65 (dd, J=11.7, 1.1 Hz, 1H), 3.47 (dd, J=17.5, 3.8 Hz), 3.32 (dd, J=11.5, 4.6 Hz), 3.21 (dd, J=17.5, 3.3 Hz, 1H), 2.2 (br s, 1H); $^{13}$C NMR (CDCl$_3$) 159.1, 142.8, 135.5, 132.6, 131.5, 128.0, 126.8, 126.0, 111.9, 111.6, 55.4, 54.5, 50.6, 47.5, 42.3; EIHRMS 251.1313 (calculated for C$_{16}$H$_{17}$ON 251.1311).

B. Synthesis of (±) 3-Chloro-IDDC

4-Chlorophenylacetyl chloride. A mixture of 4-chlorophenylacetic acid (5.00 g, 29.3 mmol) and phosphorous trichloride (2.01 g, 14.7 mmol) in a round bottom flask under nitrogen was heated to 95° C., resulting in gas evolution and a cloudy, pale yellow solution. A yellow precipitate appeared after 30 minutes, and after another 30 minutes the precipitate had congealed into an amorphous yellow solid. The remaining liquid was decanted. The solid was rinsed with methylene chloride (2×5 ml), and the rinses were combined with the decanted liquid. Concentration via rotary vaporation afforded a syrupy pale yellow residue, which was purified by vacuum distillation (short path). The acid chloride was isolated as 3.371 g of a clear colorless liquid (61% yield): b.p. 52°–530° C./0.020 torr; $^1$H NMR (CDCl$_3$) 7.30 (dd, J=44.0, 8.1 Hz, 4H), 4.14 (s, 2H).

2-(4-Chlorophenyl)-1-phenyl-1-ethanone (2). To a suspension of aluminum chloride (1.27 g, 9.52 mmol) in 30 ml dry benzene under nitrogen was added at room temperature 4-chlorophenylacetyl chloride 0.80 g, 9.52 mmol) over a period of 30 minutes as a solution in 10 ml benzene. The resulting clear, pale yellow solution was refluxed for six hours. After cooling to room temperature, the resulting grey-brown solution was poured into 100 ml ice water. The layers were separated and the aqueous portion extracted with benzene (1×20 ml). The combined organic portions were washed with water (2×30 ml), 10% NaOH (1×30 ml), water (1×30 ml), and brine (1×30 ml), and dried over magnesium sulfate. Filtration through Celite afforded, after concentration in vacuo, 2.18 g of the ketone as a white crystalline solid (99% crude yield): R$_f$ 0.46 (benzene); $^1$H NMR (CDCl$_3$) 8.03 (d, J=7.2 Hz, 2H), 7.63–7.21 (m, 7H), 4.29 (s, 2H). A portion (ca. 1 g) of the ketone was recrystallized from 75 ml boiling pet. ether/ethanol (5:1) to give a fluffy white crystalline solid: m.p. 132.5°–134.0° C. (lit. m.p. 135°–136° C.; Loeshorn, C. H. et al., J. Org. Chem. 48:4409 (1983)).

2-(4-Chlorophenyl)-1-phenyl-1-ethanone-O-methyl oxime (7). To a solution of 2-(4-chlorophenyl)-1-phenyl-1-ethanone (2, 1.93 g, 8.37 mmol) in 25 ml pyridine (dried over molecular sieves) under nitrogen was added at room temperature methoxylamine hydrochloride (873 mg, 10.5 mmol). The resulting slightly cloudy, pale orange mixture was stirred at room temperature overnight. The pyridine was removed in vacuo with heating. The residual solids were stirred with ether (60 ml), isolated by filtration, and discarded. The filtrate was dried over sodium sulfate, and concentrated in vacuo to give a mixture of the oxime geometrical isomers as 2.00 g of a clear, pale yellow syrup (92% yield). $^1$H NMR showed the isomers to be formed in a 5:3 ratio: R$_f$ 0.64, 0.50; IR (CDCl$_3$) 3068 (w), 2940 (m), 2819 (w), 1602 (w), 1493 (s), 1442 (m); $^1$H NMR (CDCl$_3$) 7.63 (m, 2H), 7.37–7.11 (m, 11.5 H), 4.12 (s, 2H), 4.05 (s, 3H), 3.91 (s, 1.6H), 3.82 (s, 1.2H); low resolution mass spec. 259 (M$^+$, 8), 227 (100), 192 (28), 165 (18), 134 (12), 125 (62), 119 (37).

2-(4-Chlorophenyl)-1-phenyl-1-amino ethane (12). To a solution of oxime geometric isomers 7 (840 mg, 3.23 mmol)

in 30 ml dry THF (freshly distilled from sodium/ benzophenone ketyl) under nitrogen was added borane-tetrahydrofuran complex (1.0M in THF, 16.2 ml, 16.2 mmol) by syringe at room temperature. The resulting pale yellow solution was refluxed overnight, and cooled in an ice bath. Water (25 ml) was carefully added to quench, followed by 20% NaOH (25 ml). The resulting bi-phasic solution was refluxed with vigorous magnetic stirring overnight. After cooling to room temperature, hexanes (40 ml) were added, and the layers were separated. The aqueous portion was extracted with hexanes (1×40 ml). The combined organic portions were dried over potassium carbonate and concentrated in vacuo to a cloudy, pale yellow syrup. This syrup was purified by column chromatography on 18 g neutral alumina (activity I) using chloroform as eluant to afford the amine as 455.6 mg of a colorless, slightly cloudy syrup (61% yield): $R_f$ 0.36 (5% ET$_2$NH/CHCl$_3$); IR (CDCl$_3$) 3376 (w), 3316 (w), 3031 (w), 2928 (m), 2856 (w), 1602 (m), 1493 (m), 1451 (m); $^1$H NMR (CDCl$_3$) δ7.38–7.28 (m, 5H), 7.26 (d, J=8.3 Hz, 2H), 7.09 (d, J=8.3 Hz, 2H), 4.18 (dd, J=8.3, 5.4 Hz, 1H), 2.98 (dd, J=13.4, 5.4 Hz, 1H), 2.84 (dd, J=13.4, 8.4 Hz), 1.50 (br s, 2H); low resolution mass spec. 232 (M$^+$, 22), 215 (37), 125 (54), 106 (100), 89 (49), 79 (100).

1-(N-ethyl-(2,2-ethoxy))-amino-1-phenyl-2-(4-chlorophenyl)ethane (17). To a solution of the amine 12 (442 mg, 1.91 mmol) in 17 ml DMF (dried over molecular sieves) was added potassium carbonate 0.053 g, 7.62 mmol) and bromoacetaldehyde diethylacetal (751 mg, 3.81 mmol, distilled) at room temperature under nitrogen. The resulting clear colorless suspension was heated at 100° C. for 20 hours. After cooling to room temperature, the reaction mixture was mixed with 10% NaOH (60 ml). The resulting yellow cloudy mixture was extracted with methylene chloride (3×30 ml). The combined organic portions were washed with water (1×30 ml) and brine (1×30 ml), and dried over potassium carbonate. Concentration in vacuo with heating afforded an orange liquid that was purified by flash chromatograph on 35 g silica gel, using 5:2 hexanes/ethyl acetate as eluant. The acetal was isolated as 332 mg of a pale orange, clear syrup (50% yield): $R_f$ 0.54 (1:1 hexanes/ethyl acetate); IR (CDCl$_3$) 3031 (w), 2977 (m), 2928 (m), 1602 (w), 1493 (m), 1451 (m), 1378 (w), 1130 (m), 1094 (m), 1057 (s); $^1$H NMR (CDCl$_3$) δ7.34–7.25 (m, 5H), 7.23 (d, J=8.4 Hz, 2H), 7.04 (d, J=8.4 Hz, 2H), 4.52 (t, J=5.6 Hz, 1H), 3.81 (t, J=7.0 Hz, 1H), 3.58 (m, 2H), 3.42 (m, 2H), 2.90 (d, J=7.0 Hz, 2H), 2.52 (m, 2H), 1.64 (s, 1H), 1.13 (dt, J=7.0, 1.3 Hz, 6H); $^{13}$C NMR (CDCl$_3$) 143.4, 137.5, 132.3, 130.8, 128.5, 127.4, 127.3, 102.1, 64.8, 62.1, 50.0, 44.7, 15.4; low resolution mass spec. 348 (M$^+$, 1), 302 (9), 227 (13), 222 (94), 215 (48), 176 (100), 130 (22), 103 (56).

(±) 3-Chloro-IDDC (22). The acetal 17 (208 mg, 0.598 mmol) and perchloric acid (1.74 g of a 69% solution, 12.0 mmol) were mixed together at room temperature under nitrogen. The resulting red-brown mixture was stirred at room temperature for 70 hours, followed by quench and basification with ice and 10% NaOH (8 ml). The resulting cloudy mixture was extracted with methylene chloride (3×8 ml), and the combined extracts were washed with brine (1×10 ml) and dried over sodium sulfate. Concentration in vacuo afforded an amber syrup, which was purified by flash chromatograph on 15 g silica gel using an elution gradient of ethyl acetate to 15% methanol/ethyl acetate (the methanol contained 1% concentrated ammonium hydroxide). 3-Chloro-IDDC was isolated as 119.0 mg of a clear, colorless syrup (76% yield): $R_f$ 0.16 (THF): IR (CDCl$_3$) 3352 (m), 3074 (m), 3025 (m), 2922 (s), 2874 (m), 1596 (s), 1487 (s), 1457 (m), 1421 (m), 1372 (m), 1251 (m), 1179 (m), 1106 (s); $^1$H NMR (CDCl$_3$) δ7.27–7.19 (m, 5H), 7.09 (dd, J=8.2, 2.2 Hz, 1H), 6.97 (d, J=8.2 Hz, 1H), 4.31 (t, J=3.7 Hz, 1H), 3.86 (d, J=4.1 Hz, 1H), 3.64 (dd, J=11.7, 1.1 Hz, 1H), 3.45 (dd, J=17.6, 3.85 Hz, 1H), 3.31 (dd, J=11.5, 4.85 Hz, 1H), 3.17 (dd, J=17.6, 3.4 Hz, 1H), 2.40 (s, 1H); $^{13}$C NMR (CDCl$_3$) 144.6, 140.8, 140.1, 133.8, 132.8, 131.3, 127.7, 127.4, 127.2, 126.7, 125.6, 125.0, 54.8, 50.5, 46.6, 41.2; EIHRMS 255.0825 (255.0816 calculated for C$_{16}$H$_{14}$NCl).

(±) 3-Chloro-IDDC maleate. To a solution of 3-chloro-IDDC (50.0 mg, 0.196 mmol) in 0.80 ml absolute ethanol was added under nitrogen maleic acid (22.7 mg, 0.196 mmol, Aldrich, used as is) as a solution in 0.30 ml ethanol at room temperature. The resulting pale brown solution was allowed to stand at room temperature for 24 hours. Addition of pentane caused, after standing overnight, the formation of a white-orange solid. This solid was re-precipitated by dissolving in ca. 2 ml boiling 1:1 benzene/ethanol, followed by pentane addition after cooling to room temperature. The maleate salt was isolated as 35.0 mg of a white solid (48% yield): m.p. 153.7°–156.0 ° C.; $^1$H NMR (MeOH-d$_4$) δ7.47–7.35 (m, 5H), 7.21 (dd, J=8.2, 2.1 Hz, 1H), 7.10 (d, J=8.3 Hz, 1H), 6.24 (s, 2H), 4.99 (t, J=3.0 Hz, 1H), 4.26 (d, J=4.2 Hz, 1H), 3.87 (d, J=12.5 Hz, 1H), 3.69 (dd, J=18.7, 3.0 Hz, 1H), 3.53 (dd, J=12.5, 4.6 Hz, 1H), 3.33 (dd, J=18.4, 3.0 Hz, 1H).

C. Synthesis of (±) 3-Bromo-IDDC

4-Bromophenylacetyl chloride. A mixture of 4-bromophenylacetic acid (6.00 g, 27.9 mmol, Aldrich, used as is) and phosphorous trichloride (1.92 g, 14.0 mmol, Aldrich, used as is) was heated under nitrogen to 100° C. After one hour, the resulting cloudy liquid was decanted from an amorphous yellow solid. The solid was rinsed with methylene chloride (2×5 ml), and the rinses were combined with the decanted liquid. Rotary evaporation of the resulting solution afforded a slightly yellow syrup, which was purified by vacuum distillation (short path) to afford the acid chloride as 4.65 g of a clear, very pale yellow liquid (71% yield): b.p. 56.5–59.5° C./0.025 torr; $^1$H NMR δ7.52 (d, J=8.4 Hz, 2H), 7.17 (d, J=8.4 Hz, 2H), 4.13 (s, 2H).

2-(4-Bromophenyl)-1-phenyl-1-ethanone (3). To a suspension of aluminum chloride (2.64 g, 19.8 mmol) in dry benzene (40 ml) was added a solution of 4-bromophenylacetyl chloride (4.63 g, 19.8 mmol) in 15 ml benzene over a period of 25 minutes under nitrogen. The resulting dark yellow solution was refluxed for six hours, and cooled to room temperature. Ice water (100 ml) was added, and the layers separated. The aqueous layer was extracted with benzene (1×50 ml). The combined organic portions were washed with water (2×60 ml), 10% NaOH (1×60 ml), water (1×60 ml), and brine (1×60 ml), and dried over magnesium sulfate. After filtration, concentration of the filtrate in vacuo afforded the ketone as 5.06 g of a white microcrystalline solid (93% yield). NMR indicated good purity. A portion was recrystallized from boiling petroleum ether/ethanol to give the ketone as colorless plates: m.p. 147.5°–149.0° C. (lit. m.p. 146°–147° C.; Huttel, R. et al., *J. Chem. Ber.* 93:1433 (1960)); $^1$H NMR δ8.02 (d, J=7.1 Hz, 2H), 7.63–7.46 (m, 5H), 7.16 (d, J=8.3, 2H), 4.27 (s, 2H).

2-(4-Bromophenyl)-1-phenyl-1-ethanone-O-methyl oxime (8). To a solution of 2-(4-bromophenyl)-1-phenyl-1-ethanone (3, 4.55 g, 16.5 mmol) in 65 ml pyridine (dried over molecular sieves) was added methoxylamine hydrochloride (1.66 g, 19.8 mmol, Aldrich, used as is) at room temperature. The resulting yellow-orange, slightly turbid mixture was stirred at room temperature for 20 hours, and the pyridine was removed in vacuo with heating. The residue was stirred with ether (60 ml), followed by filtration. The filtrate was dried over sodium sulfate, and concentrated to a syrupy orange residue. This residue was purified by column chromatography on 20 g alumina (neutral, activity I) using benzene as eluant. The mixture of geometric isomers was isolated as 4.953 g of a clear, pale amber syrup (98% yield). $^1$H NMR indicated that the isomers were formed in a 1.65:1 ratio: R$_f$ 0.57, 0.46 (benzene): IR (CDCl$_3$) 3068 (w), 2971 (m), 2940 (m), 2898 (m), 2819 (m), 1602 (w), 1487 (s), 1463 (m), 1439 (m), 1403 (m), 1330 (m), 1191 (w), 1106 (m), 1072 (m), 1047 (s), 1022 (m), 1013 (s); $^1$H NMR (CDCl$_3$) δ7.64 (m, 2H), 7.43–7.25 (m, 8.5 H), 7.10 (2d, J=8.4 Hz, 3H), 4.11 (s, 2H), 4.05 (s, 3H), 3.92 (s, 1.8 H), 3.81 (s, 1.25H); low resolution mass spec. 305 (M$^+$, 5.8), 303 (M$^+$, 5.8), 273 (100), 271 (100), 192 (44), 171 (45), 169 (45), 165 (34), 135 (18), 119 (67), 103 (44).

1-Amino-2-(4-bromophenyl)-1-phenylethane (13). To a solution of the mixture of oxime isomers 8 (4.92 g, 16.2 mmol) in 75 ml THF (freshly distilled from sodium benzophenone ketyl) under nitrogen was added borane-tetrahydrofuran complex (1.0M in THF, 55.0 ml, 55.0 mmol) by syringe at room temperature. The resulting pale orange solution was brought to reflux and held there for 16 hours. With cooling by an ice bath, water (125 ml) was carefully added to quench, followed by 20% NaOH (125 ml).The resulting biphasic solution was refluxed with vigorous magnetic stirring overnight. After cooling to room temperature, hexanes (60 ml) were added and the layers were separated. The aqueous portion was extracted with hexanes (2×50 ml). The combined organic portions were dried over potassium carbonate and concentrated in vacuo to a cloudy, colorless syrup. This syrup was purified by column chromatography on 20 g neutral alumina (activity I) using a 20% ethyl acetate-hexanes to 4% diethylamine-chloroform elution gradient. The amine 13 was isolated as 3.985 g of a clear, colorless syrup (89% yield): R$_f$ 0.18 (2% diethylamine in CHCl$_3$); $^1$H NMR (CDCl$_3$) δ7.41 (d, J=8.2 Hz, 2H), 7.35–7.28 (m, 5H), 7.03 (d, J=8.2 Hz, 2H), 4.18 (dd, J=8.2, 5.3 Hz, 1H), 2.97 (dd, J=13.3, 53 Hz, 1H), 2.83 (dd, J=13.3, 8.3 Hz, 1H), 1.45 br s, 2H); low resolution mass Spec. 277 (M$^+$, 1.5), 275 (M$^+$, 1.5), 261 (2.2), 259 (2.2), 171, (4.5), 169 (4.5), 106 (100), 79 (45).

1-(N-ethyl-(2,2-ethoxy))-amino-1-phenyl-2-(4-bromophenyl)ethane (18). To a solution of the amine 13 (3.97 g, 14.4 mmol) in DMF (125 ml, dried over molecular sieves) under nitrogen was added potassium carbonate (7.96 g, 57.6 mmol) and bromoacetaldehyde diethylacetal (7.09 g, 36.0 mmol, distilled) at room temperature. The resulting clear colorless mixture was heated to 100° C. and held there for 16 hours. After cooling to room temperature, 10% NaOH (225 ml) was added. The resulting cloudy mixture was extracted with methylene chloride (3×85 ml). The combined extracts were washed with water (1×100 ml) and brine (1×100 ml), and dried over potassium carbonate. Concentration in vacuo with heating afforded a clear red syrup, which was purified by flash chromatography on 45 g silica gel, using a hexanes to 20% ethyl acetate/hexanes elution gradient. The acetal 18 was isolated as 3.709 g of a red-orange syrup (65% yield): R$_f$ 0.312 (hexanes/ethyl acetate 2:1); IR (CDCl$_3$) 3322 (w), 3068 (w), 3031 (w), 2977 (m), 2928 (m), 1487 (s), 1451 (m), 1378 (m), 1130 (s), 1063 (s), 1015 (m); $^1$H NMR (CDCl$_3$) δ7.39–7.22 (m, 7H), 6.98 (d, J=8.35 Hz, 2H), 4.52 (t, J=5.6 Hz, 1H), 3.81 (t, J=7.0 Hz, 1H), 3.58 (m, 2H), 3.43 (m, 2H), 2.89 (d, J=7.0 Hz, 2H), 2.53 (m, 2H), 1.63 (br s, 1H), 1.13 (dr, J=7.0, 1.1 Hz, 6H); low resolution mass spec. 394 (M$^+$1, 60), 392 (M+1, 61), 348 (26), 346 (27), 261 (11), 259 (11), 222 (97), 176 (100).

(±) 3-Bromo-IDDC (23). To the neat acetal 18 (365.0 mg, 0.9303 mmol) at room temperature under nitrogen was added perchloric acid (2.71 g of a 69% solution, 18.6 mmol) by syringe. The resulting cloudy grey-brown mixture was stirred at room temperature for 27 hours. Cracked ice was added, followed by 10% NaOH (10 ml) so that the pH>10. The resulting cloudy white mixture was extracted with methylene chloride (3×10 ml). The combined extracts were washed with brine (1×15 ml) and dried over sodium sulfate. Concentration in vacuo afforded an amber residue, which was purified by flash chromatography on 15 g silica gel using an ethyl acetate to 10% methanol/ethyl acetate elution gradient (the methanol itself contained 1% concentrated ammonium hydroxide). The product was isolated as 162.4 mg of a clear, very pale brown syrup that solidified upon standing (58% yield): m.p. 87.5°–90.0° C.; R$_f$ 0.26 (ethyl acetate/methanol 4:1); IR (CDCl$_3$) 3352 (w), 3080 (w), 3025 (w), 2922 (m), 2874 (w), 1590 (m), 1481 (s), 1457 (m), 1421 (m), 1372 (w), 1251 (m), 1179 (m), 1112 (m); $^1$H NMR δ7.37 (d, J=2.0 Hz, 1H), 7.30–7.15 (m, 5H), 6.90 (d, J=8.2 Hz, 1H), 4.30 (t, J=3.7 Hz, 1H, 3.84 (d, J=4.5 Hz, 1H), 3.62 (d, J=11.2, 1H), 3.43 (dd, J=17.6, 3.8 Hz, 1H), 3.28 (dd, J=11.5, 4.8 Hz, 1H), 3.14 (dd, J=17.6, 3.4 Hz, 1H), 2.10 (s, 1H); $^{13}$C NMR (CDCl$_3$) 145.4, 141.1, 140.5, 134.8, 133.4, 130.9, 129.9, 127.7, 127.5, 126.0, 125.3, 119.6, 55.1, 51.9, 46.8, 41.6; low resolution mass spec. 301 (M$^+$, 15), 300 (16), 299 (M$^+$, 15), 299 (15), 298 (16), 273 (7), 272 (37), 271 (13), 270 (37), 269 (8), 191 (22), 189 (23), 130 (100).

(±) 3-Bromo-IDDC Maleate. To a solution of 3-bromo-IDDC (72.0 mg, 0.240 mmol) in 0.60 ml absolute ethanol under nitrogen was added a solution of maleic acid (27.8 g, 0.240 mmol, Aldrich, used as is) in 0.30 ml ethanol at room temperature; 0.20 ml ethanol was used as rinse. The resulting pale brown solution was allowed to stand at room temperature overnight. No precipitate was present. Pentane (1 ml) was added, resulting in cloudiness in the solution. After standing overnight, a white precipitate had formed, which was collected as 90.0 mg of small white pebbles after rinsing with dry ether and drying in vacuo (90% yield): m.p. 165.0°–167.5° C.; $^1$H NMR (CD$_3$OD) δ7.53 (d, J=2.0 Hz, 1H), 7.48–7.32 (m, 5H), 7.04 (d, J=8.3 Hz, 1H), 6.24 (s, 2H), 4.98 (t, J=3.6 Hz, 1H), 4.25 (d, J=4.5 Hz, 1H), 3.86 (d, J=12.4 Hz, 1H), 3.66 (dd, J=18.8, 3.3 Hz, 1H), 3.53 (dd, J=12.4, 4.85 Hz, 1H), 3.28 (dd, J=18.7, 3.2 Hz, 1H).

D. Synthesis of (±) N-Methyl-3-bromo-IDDC

The procedure of Borch and Hassid was adapted. (Borch et al, *J. Org. Chem.* 37:1673 (1972)). To a solution of 3-bromo-IDDC (68.1 mg, 0.227 mmol) in acetonitrile (0.50 ml, dried over molecular sieves) at room temperature was added aqueous formaldehyde (37% solution, 0.065 ml, 0.87 mmol). A white solid formed immediately. Sodium cyanoborohydride (20.0 mg, 0.318 mmol, Aldrich, used as is) was introduced. A mild exotherm was observed, and the solid gradually dissolved. The resulting cloudy yellow mixture was stirred for 30 minutes, and glacial acetic acid (2 drops) was added to bring the pH to ca. 6 (by wet pH paper). Stirring was continued; after 10 minutes more acetic acid (2 drops) was added to maintain the pH near neutral. Stirring was continued for 40 more minutes, during which the pH remained constant. The reaction mixture was concentrated in vacuo to a pale yellow residue, which was taken up in methylene chloride (10 ml) and 10% NaOH (5 ml). The layers were separated and the organic layer washed with 10% NaOH (2×10 ml) and brine (1×10 ml), and dried over potassium carbonate. Evaporation of the solvent afforded a white residue, which was purified by preparative thin layer chromatography (1000 micron thickness, silica gel) using 8% methanol/ethyl acetate as eluant (the methanol contained 1% concentrated ammonium hydroxide). The N-methyl amine was isolated as 49 mg of a clear colorless residue (69% yield): $R_f$ 0.36 (ethyl acetate/methanol 4:1); $^1H$ (CDCl$_3$) δ7.33 (d, J=1.9 Hz, 1H), 7.24–7.15 (m, 5H), 6.91 (d, J=8.2 Hz, 1H), 3.96 (t, J=3.6 Hz, 1H), 3.60 (d, J=3.8 Hz, 1H), 3.60 (dd, J=10.8, 1.1 Hz, 1H), 3.57 (dd, J=17.4, 4.0 Hz, 1H), 2.94 (dd, J=17.5, 3.0 Hz, 1H), 2.91 (dd, J=10.7, 4.6 Hz, 1H), 2.50 (s, 3H). Low resolution mass spec. 315(M$^+$+1, 17), 314(M$^+$, 23), 313(M$^+$+1, 17), 312(M$^+$, 20), 272(17), 270(18), 192(4.3), 191(16), 190(8.7), 189(20), 144(100), 145(28).

E. Synthesis of (±) 7-Chloro-IDDC 1-(4-Chlorophenyl)-1-phenyl-1-ethanone (4). The procedure of Newman and Reid was followed. (Newman et al., *J. Org. Chem.* 23:665 (1958)). To a slurry of aluminum chloride (5.84 g, 43.8 mmol) in chlorobenzene (17.2 ml, 169 mmol, freshly distilled from calcium hydride) was added at room temperature phenylacetyl chloride (6.15 g, 39.8 mmol) via syringe. An exotherm resulted and the reaction mixture turned orange. The reaction mixture was heated at 70° C. for 90 minutes, and poured onto cracked ice. The solid product was solubilized in methylene chloride, and the layers were separated. The aqueous portion was extracted with methylene chloride (30 ml, 2×). The combined organic portions were washed with 10% NaOH (30 ml, 1×), water (30 ml, 1×) and brine (30 ml, 1×), and dried over magnesium sulfate. After filtration through celite, concentration of the filtrate afforded a moist orange solid. This solid was recrystallized twice, first from 4:1 ethanol-water and then from absolute ethanol to give the ketone as 3.63 g of a pale orange powder (40% yield): m.p. 85°–90° C.; $^1H$ NMR ((CDCl$_3$) 7.98 (d, J=8.4 Hz, 2H), 7.45 (d, J=8.6 Hz, 2H), 7.39–7.23 (m, 5H), 4.28 (s, 2H).

1-(4-Chlorophenyl)-2,-phenyl-1-ethanone-O-methyl oxime (9). To a solution of 1-(4-chlorophenyl)-2-phenyl-1-ethanone (4, 2.71 g, 11.7 mmol) in pyridine (45 ml, dried over molecular sieves) under nitrogen was added methoxylamine hydrochloride (1.273 g, 15.24 mmol, Aldrich, used as is) at room temperature. The resulting pale orange solution was stirred at room temperature overnight. The pyridine was evaporated with mild heating. The residual solids were stirred with ether (75 ml), and the resulting suspension was filtered. Evaporation of the solvent afforded an orange syrup, which was purified by column chromatography on neutral alumina (activity I, 15 g) using benzene as eluant. The mixture of syn- and anti-isomers was isolated as 2.781 g of a clear, pale orange syrup (89% yield). NMR analysis indicated that the isomers were formed in a 1.6:1 ratio: $R_f$ 0.58, 0.40 (benzene): IR (CDCl$_3$) 3.68 (w), 3031 (w), 2940 (m), 2898 (w), 2819 (w), 1602 (m), 1493 (s), 1451 (m), 1094 (s), 1045 (s), 1015 (m); $^1H$ NMR (CDCl$_3$) δ7.60 (d, J=8.6 Hz, 2H), 7.40–7.17 (m, 12 H), 4.15 (s, 2H), 4.06 (s, 3H), 3.93 (s, 1.75 H), 3.84 (s, 1.35 H); low resolution mass spec. 261 (M$^+$, 5.6), 259 (M$^+$, 10), 229 (39), 227 (99), 192 (30), 165 (29), 153 (33), 137 (31), 91 (100).

1-Amino-1-(4-chlorophenyl)-2-phenylethane (14). To a solution of the oxime geometric isomer mixture 9 (2.690 g, 10.36 mmol) in dry THF (50 ml, freshly distilled from sodium benzophenone ketyl) under nitrogen at room temperature was added borane-tetrahydrofuran solution (36.0 ml, 36.0 mmol, 1.0M solution, Aldrich) by syringe. The resulting very pale orange solution was refluxed for 16 hours, and cooled in an ice bath. Water (80 ml) was added carefully to quench, followed by 20% NaOH (80 ml). The resulting colorless bi-phasic mixture was refluxed overnight with vigorous magnetic stirring. After cooling to room temperature, hexanes (50 ml) were added and the layers separated. The aqueous portion was washed with hexanes (1×30 ml), and the combined organic portions dried over potassium carbonate. Evaporation of the solvent afforded the pure amine as 2.392 g of a clear, pale yellow syrup (99% yield): $R_f$ 0.22 (5% methanol in CHCl$_3$): IR (CDCl$_3$) 3376 (w), 3068 (w), 3031 (w), 2922 (w), 2850 (w), 1602 (m), 1493 (s), 1457 (m), 1409 (w); $^1H$ NMR (CDCl$_3$) δ7.40–21 (m, 7H), 7.19 (d, J=8.6 Hz, 2H), 4.21 (dd, J=8.4, 5.2 Hz, 1H), 2.98 (dd, J=13.2, 5.2 Hz, 1H), 2.81 (dd, J=13.2, 8.6 Hz, 1H), 1.43 (s, 2H); low resolution mass spec. 232 (M–1, 5.0), 230 (m–1, 11), 142 (M–91, 37), 140 (M–91, 100), 91 (28).

1-(N-ethyl-(2,2-ethoxy))-amino-1-(4-chloro-phenyl)-2-phenylethane (19). To a solution of 1-amino-1-(4-chlorophenyl)-2-phenylethane (14, 2.392 g, 10.32 mmol) in dry DMF (95 ml, dried over molecular sieves) under nitrogen was added bromoacetaldehyde diethylacetal (5.09 g, 25.8 mmol, distilled), and potassium carbonate (5.71 g, 41.3 mmol) at room temperature. The resulting very pale yellow suspension was immersed in an oil bath at 100° C. and held there for 18 hours. After cooling to room temperature, to the resulting pea-green slurry was added 10% NaOH (150 ml). The resulting pale brown mixture was extracted with methylene chloride (3×50 ml); the combined organic extracts were washed with water (1×100 ml) and brine (1×75 ml), and dried over potassium carbonate. After filtration, evaporation of the solvent (with mild heating to drive off the residual DMF) afforded a thick red syrup. This syrup was purified by flash chromatography on silica gel (38 g) using an elution gradient of hexanes to 15% ethyl acetate/hexanes. The acetal was isolated as 2.486 g of a clear, pale orange syrup (69% yield): $R_f$ 0.40 (hexanes/ethyl acetate 2:1); IR (CDCl$_3$) 3031 (w), 2983 (m), 2910 (m), 1493 (m), 1457 (m), 1378 (m), 1124 (m), 1094 (s), 1057 (s); $^1H$ (CDCl$_3$) δ7.32–7.21 (m, 7H), 7.12 (d, J=6.7 Hz, 2H), 4.50 (t, J=5.6 Hz, 1H), 3.83 (dd, J=7.5, 6.6 Hz, 1H), 3.62–3.49 (m, 2H), 3.49–3.34 (m, 2H), 2.95–2.80 (m, 2H), 2.58–2.42 (m, 2H), 1.67 (s, 1H), 1.11 (q, J=6.7 Hz, 6H); low resolution mass spec. 350 (M+1, 3.4), 348 (M+1, 9.0), 304 (4.5), 302 (13), 258 (30), 256 (80), 215 (51), 212 (36), 210 (92), 125 (46), 103 (100), 91 (29).

7-Chloro-IDDC (24). To the neat acetal 19 (145.4 mg, 0.4180 mmol) at room temperature was added concentrated sulfuric acid (820 mg, 8.36 mmol). The resulting red mixture was stirred at room temperature for 40 hours. Cracked ice was added, followed by 10% NaOH until pH>10. The resulting cloudy mixture was extracted with methylene chloride (3×8 ml). The combined organic extracts were washed with brine (1×20 ml), and dried over potassium carbonate. Evaporation of the solvent afforded a dark golden syrup, which was purified by flash chromatography on silica gel (3.2 g) using an elution gradient of ethyl acetate to 15% methanol/ethyl acetate (the methanol itself was 1% concentrated ammonium hydroxide). The product was isolated as 29.9 mg of a clear, pale yellow syrup (31% yield): $R_f$ 0.19 (ethyl acetate-methanol 4:1); IR (CDCl$_3$) 3352 (w), 3062 (w), 3019 (m), 2922 (s), 1874 (m), 1602 (m), 1578 (w), 1499 (m), 1481 (s), 1451 (m), 1415 (m), 1269 (w), 1179 (w), 1082 (m); $^1H$ NMR δ7.25–7.04 (m, 7H), 4.33 (t, J=3.6 Hz, 1H), 3.88 (d, J=4.4 Hz, 1H), 3.66 (dd, J=11.4, 1.0 Hz, 1H), 3.49 (dd, J=17.6, 3.8 Hz, 1H), 3.31 (dd, J=11.4, 4.7 Hz, 1H), 3.20 (dd, J=17.6, 3.4 Hz, 1H), 2.06 (s, 1H); $^{13}C$ NMR (CDCl$_3$) 143.2, 142.3, 138.8, 135.1, 132.7, 131.4, 128.0, 127.0, 126.8, 126.3, 126.1, 125.7, 54.6, 50.5, 46.9, 41.7. Low resolution mass. spec. 257(M+1, 12), 256(M, 18), 255(M+1, 33), 254(M, 30), 228(25), 226(61), 191(29), 189(25), 166 (32), 164(100).

F. Synthesis of (±) 3-Methoxy-IDDC 2-(4-Methoxyphenyl)-1-phenyl-1-ethanone (5). To a suspension of aluminum chloride (2.71 g, 20.3 mmol) in benzene (55 ml, dried over sodium) under nitrogen was added dropwise a solution of 4-methoxyphenylacetyl chloride (3.753 g, 20.33 mmol, prepared in 42% yield from 4-methoxyphenylacetic acid and phosphorous trichloride) in 20 ml benzene over a period of 30 minutes at room temperature. The resulting slightly cloudy, pale brown mixture was refluxed for four hours, and poured into 150 ml ice water. The layers were separated and the aqueous phase extracted with benzene (1×50 ml). The combined organic portions were washed with water (1×75 ml), 10% NaOH (1×75 ml), water (1×75 ml), and brine (1×75 ml), and dried over magnesium sulfate. Following filtration through Celite, the filtrate was evaporated to 2.60 g of pale yellow plates (56% crude yield). This solid was recrystallized from boiling 25% ethanol/petroleum ether to give the ketone as a pale yellow powder: m.p. 87°–92° C. (lit. m.p. 96°–97° C.; Schneider, M. R. et al, *J. Med. Chem.* 25:1070 (1982)); $^1$H NMR (CDCl$_3$) δ8.03 (d, J=7.3 Hz, 2H), 7.62–7.45 (m, 3H), 7.20 (d, J=8.6 Hz, 2H), 6.89 (d, J=8.6 Hz, 2H), 4.25 (s, 2H), 3.8 (s, 3H).

2-(4-Methoxyphenyl)-1-phenyl-1-ethanone-O-methyl oxime (10). To a solution of 2-(4-methoxyphenyl)-1-phenyl-1-ethanone (5, 1.77 g, 7.82 mmol) in pyridine (30 ml, dried over molecular sieves) under nitrogen was added methoxylamine hydrochloride (784 mg, 9.39 mmol, Aldrich, used as is) at room temperature. The resulting pale yellow solution was stirred at room temperature overnight The pyridine was evaporated with mild heating. The residual solids were stirred with ether (50 ml), and the resulting suspension was filtered. The filtrate was dried over potassium carbonate, and the solvent evaporated to give a clear, pale yellow syrup. This syrup was purified by column chromatography on 20 g neutral alumina (activity I) using 3% ethyl acetate/toluene as eluant. The oxime was isolated as 1.664 g of a clear colorless syrup (83% yield). NMR analysis indicated that the syn- and anti-isomers were formed in a 3:1 ratio: R$_f$ 0.65, 0.55 (5% ethyl acetate/benzene); IR (CDCl$_3$) 2989 (w), 947 (w), 2904 (w), 2838 (w), 2819 (w), 1614 (m), 1512 (s), 1245 (s), 1039 (w); $^1$H NMR (CDCl$_3$) δ7.83 (m, 1H), 7.37–7.23 (m, 4H), 7.15 (d, J=8.6 Hz, 1H), 7.10 (d, J=8.6 Hz, 1H), 6.80 (t, J=8.4 Hz, 2H), 4.10 (s, 1H), 4.05 (s, 1.5H), 3.91 (s, 1H), 3.78 (s, 3H). Low resolution mass spec. 255(M, 16), 224(26), 223 (100), 209(19), 208(89), 121(100).

1-Amino-2-(4-methoxyphenyl)-1-phenylethane (15). To a solution of a mixture of syn-and anti-isomers of 2-(4-methoxyphenyl)-1-phenyl-1-ethanone-O-methyl oxime (10, 1.65 g, 6.46 mmol) in THF (40 ml, freshly distilled from sodium benzophenone ketyl) under nitrogen was added borane-tetrahydrofuran solution (21.2 ml, 21.2 mmol, 1.0M solution, Aldrich) at room temperature. The resulting pale yellow solution was refluxed overnight, and cooled in an ice water bath. Water (50 ml) was carefully added to quench, followed by 20% NaOH (50 ml). The resulting colorless bi-phasic mixture was refluxed with vigorous magnetic stirring overnight, and allowed to cool to room temperature. Hexanes (40 ml) were added, and the layers separated. The aqueous portion was extracted with hexanes (1×40 ml). The combined organic portions were dried over potassium carbonate, and concentrated in vacuo to afford a colorless, slightly cloudy syrup. This syrup was purified by column chromatography on neutral alumina (I, 15 g) using an elution gradient of chloroform to 10% methanol/chloroform. The amine 15 was isolated as 1.263 g of a clear, colorless syrup (86% yield): R$_f$ 0.20 (5% methanol/chloroform); IR (CDCl$_3$) 3376 (w), 3316 (w), 3068 (w), 3031 (w), 3007 (w), 2965 (m), 2940 (m), 2910 (m), 2834 (m), 1614 (m), 1584 (m), 1514 (s), 1493 (m), 1466 (m), 1454 (m), 1441 (m), 1300 (m), 1245 (s), 1179 (m), 1106 (w), 1033 (m); $^1$H NMR (CDCl$_3$) δ7.40–7.24 (m, 5H), 7.11 (d, J=8.6 Hz, 2H), 6.85 (d, J=8.6 Hz, 2H), 4.18 (dd, J=8.6, 4.9 Hz, 1H), 3.81 (s, 3H), 2.98 (dd, J=13.5, 4.9 Hz, 1H), 2.79 (dd, J=13.5, 8.7), 1.49 (s, 2H). Low resolution mass spec. 228(M+1, 26), 211(49), 121(44), 107(69), 106(100), 79(100).

1-(N-ethyl-(2,2-ethoxy))-amino-2-(4-methoxyphenyl)-1-phenylethane (20). To a solution of the amine 15 (1.246 g, 5.482 mmol) in DMF (50 ml, dried over molecular sieves) under nitrogen at room temperature was added bromoacetaldehyde diethylacetal (2.70 g, 13.7 mmol, distilled) and potassium carbonate (3.03 g, 21.2 mmol). The resulting clear colorless suspension was immersed in an oil bath at 100° C. After 23 hours, the resulting yellow reaction mixture was allowed to cool to room temperature and mixed with 10% NaOH (100 ml). The resulting cloudy mixture was extracted with methylene chloride (3×40 ml). The combined extracts were washed with water (5×60 ml, NaCl was used to break up emulsions in the later extractions) and brine (1×50 ml), and dried over potassium carbonate. Concentration in vacuo with mild heating (<50° C.) afforded a golden syrup, which was purified by flash chromatography on 30 g silica gel using an elution gradient of hexanes to 12% ethyl acetate/hexanes. The acetal 20 was isolated as 1.316 g of a clear, pale yellow syrup (70% yield): R$_f$ 0.39 (hexanes/ethyl acetate 2:1); IR (CDCl$_3$) 3340 (w), 3031 (w), 2983 (m), 2934 (w), 2910 (w), 2838 (w), 1614 (m), 1512 (s), 1467 (m), 1454 (m), 1444 (m), 1376 (w), 1303 (w), 1247 (s), 1177 (m), 1126 (m), 1061 (m), 1035 (m); $^1$H NMR (CDCl$_3$) δ7.36–7.23 (m, 5H), 7.06 (d, J=8.5 Hz, 2H), 6.82 (d, J=8.4 Hz, 2H), 4.52 (t, J=5.7 Hz, 1H), 3.80 (s, 3H), 3.8 (m, 1H, hidden under the singlet at 3.80), 3.56–3.50 (m, 2H), 3.49–3.42 (m, 2H), 2.98–2.89 (m, 2H), 2.55–2.47 (m, 2H), 1.68 (s, 1H), 1.11 (dt, J=7.0, 4.2 Hz, 6H). pending. Low resolution mass. spec. 344(M+1, 33), 298(16), 222(63), 211(43), 176(100), 121(57), 91(90).

(±) 3-Methoxy-IDDC (25). To the neat acetal 20 (219.2 mg, 0.6382 mmol) under nitrogen at room temperature was added perchloric acid (69% solution, 1.28 g, 12.8 mmol). The resulting dark yellow solution was stirred at room temperature. After 64 hours, the reaction mixture was a clear, pale brown gel. Cracked ice was added, followed by 10% NaOH (15 ml). A cloudy white mixture resulted, along with an amorphous yellow solid. The whole was extracted with methylene chloride (3×8 ml); the yellow solid did not dissolve. The combined organic extracts were washed with brine (1×10 ml) and dried over potassium carbonate. Concentration in vacuo afforded 136 mg of a pale brown foam. This foam was purified by flash chromatography on 4.0 g silica gel using an elution gradient of ethyl acetate to 20% methanol/ethyl acetate (the methanol contained 1% concentrated ammonium hydroxide). The desired product 25 was isolated as 18.2 mg of a clear, colorless syrup (11% yield): R$_f$ 0.17 (ethyl acetate/methanol 4:1); $^1$H NMR (CDCl$_3$) δ7.2 (br s, 4H), 6.97 (d, J=8.4 Hz, 1H), 6.75 (d, J=2.4 Hz), 6.70 (d, J=2.5 Hz), 6.67 (d, J=2.6 Hz, 2H over 6.75–6.67), 4.33 (t, J=3.6 Hz, 1H), 3.86 (d, J=4.2 Hz, 1H), 3.79 (S, 3H), 3.66 (d, J=11.8 Hz, 1H), 3.43 (dd, J=17.2, 3.7 Hz, 1H), 3.32 (dd, J=11.5, 4.7 Hz, 1H), 3.16 (dd, J=17.2, 3.3 Hz, 1H), 2.12 (s, 1H). $^{13}$C NMR (CDCl$_3$): 157.8, 144.1, 141.3, 140.4, 132.4, 127.2, 127.1, 126.8, 125.5, 124.9, 113.6, 112.2, 55.3, 55.2, 50.7, 47.3, 41.0; low resolution mass spec. 251(M, 31), 250(23), 222(66), 179(34), 178(31), 130(100).

G. Synthesis of (±) 3-Chloro-7-methoxy-IDDC 2-(4-Chlorophenyl)-1-(4-methoxyphenyl)-1-ethanone. 4-Chlorophenylacetyl chloride was prepared as described before. To a suspension of aluminum chloride (1.27 g, 9.52 mmol) and anisole (1.4 g, 12.9 mmol) in $CH_2Cl_2$ (40 ml) under nitrogen was added 4-chlorophenylacetyl chloride (1.8 g, 9.52 mmol) over a period of 30 minutes as a solution in $CH_2Cl_2$ at room temperature. The resulting clear, pale yellow solution was refluxed for 18 hours. After cooling to room temperature, the resulting solution was poured into 100 ml ice water. The layers were separated and the aqueous portion was extracted with methylene chloride (50 ml, 2 times). The combined organic layers were washed with water (50 ml, 2 times), 10% NaOH (30 ml, 2 times), water (30 ml, 2 times), and brine (40 ml). The organic solution was further dried over $MgSO_4$, filtered, and concentrated to yield a white solid (2.45 g, 99% yield). $R_f$: 0.41 ($CH_2Cl_2$).

2-(4-Chlorophenyl)-1-(4-methoxyphenyl)-1-ethanone-O-methyl oxime. To a solution of 2-(4-chlorophenyl)-1-(4-methoxyphenyl)-1-ethanone (1.386 g, 5.3 mmol) in 10 ml pyridine under nitrogen was added methoxylamine hydrochloride (0.664 g, 7.96 mmol) at 25° C. The resulting mixture was stirred at 20° C. for 17 hours. The pyridine was removed in vacuo with heating. The residual solids were a mixture of the oxime geometrical isomers as a white syrup (1.41 g, 92% yield). $R_f$: 0.45, 0.64 ($CH_2Cl_2$).

1-Amino-2-(4-chlorophenyl)-1-(4-methoxyphenyl) ethane. To a solution of 2-(4-chlorophenyl)-1-(4-methoxyphenyl)-1-ethanone-O-methyl oxime (1.34 g, 4.62 mmol) in 30 ml dry THF under nitrogen was added borane-THF complex (1.0M in THF, 23.1 ml, 23.1 mmol) by syringe at 25° C. The resulting bi-phasic solution was refluxed with vigorous magnetic stirring for 16 hours. After the reaction was cooled to 25° C., quenched with 10% NaOH solution, hexanes (50 ml) were added and the layers were separated. The aqueous portion was extracted with hexanes again (40 ml). The combined organic layers were dried over magnesium sulfate and concentrated in vacuo to yield a cloudy colorless syrup (1.18 g, 98% yield). $R_f$: 0.32 ($CH_2Cl_2$/MeOH 20:1).

1-(N-Ethyl-(2,2-ethoxy))-amino-1-(4-methoxyphenyl)-2-(4-chlorophenyl)-ethane. To a stirred mixture of 1-amino-2-(4-chlorophenyl)-1-(4-methoxyphenyl)ethane (340 mg, 1.3 mmol) and anhydrous potassium carbonate (193.5 mg, 1.4 mmol) in 2.5 ml of N,N-dimethylformamide was added dropwise a solution of bromoacetaldehyde diethylacetal (276 mg, 1.4 mmol) at 90° C. The resulting mixture was heated with stirring. After 18 hours the reaction mixture was cooled to 10° C., 50 ml of $^1$N NaOH was added followed by 25 ml of $CH_2Cl_2$. The layers were separated and the aqueous layer was extracted with $CH_2Cl_2$ (15 ml, two times). The combined organic layers were washed with NaOH (1N, 10 ml) and water (50 ml, 10 times), dried ($K_2CO_3$), and concentrated to yield the crude product. The crude product (450 mg) was chromatographed (20 g silica gel) using $CH_2Cl_2$ followed by $CH_2Cl_2$/THF (20:1) then $CH_2Cl_2$/THF (5:1) as eluent. The pure product was obtained as a white solid (386 mg, 89% yield). $R_f$: 0.58 ($CH_2Cl_2$/THF 1:5). $^1$H NMR ($CDCl_3$): δ7.22 (m, 2H, phenyl), 7.05 (d, 1H, J=8.4 Hz, phenyl), 6.87 (d, 1H, J=8.6 Hz, phenyl), 4.53 (t, 1H, J=5.5 Hz, 1H), 3.83 (s, 3H, $CH_3$), 3.60 (m, 2H, $CH_2$), 3.44 (m, 2H, $CH_2$), 2.77 (t, 1H, J=7.0 Hz, CH), 2.90 (d, 2H, J=7.0 Hz, $CH_2$), 2.54 (m, 2H, $CH_2$), 1.65 (br., 1H, NH), 1.15 (t, 6H, J=7.0 Hz, $CH_3$). $^{13}$C NMR ($CDCl_3$): 137.56, 135.41, 132.19, 130.74, 128.42, 128.37, 113.92, 102.07, 64.10, 62.07, 62.12, 55.33, 49.97, 44.70, 15.35.

3-Chloro-7-methoxy-IDDC. 1-(N-Ethyl-(2,2-ethoxy))-amino-1-(4-methoxyphenyl)-2-(4-chlorophenyl)ethane (180 mg, 0.54 mmol) and perchloric acid (5 ml of 70% solution) were mixed together at room temperature under nitrogen. The resulting white mixture was stirred at ice and 10% NaOH. The resulting cloudy mixture was extracted with room temperature for 60 hours, followed by quench and basification with ice and 10% NaOH. The resulting cloudy mixture was extracted with methylene chloride (2.5 ml, 3 times), and the combined extracts were washed with brine (10 ml) and dried over sodium sulfate. Concentration in vacuo afforded an amber syrup, which was purified by prep. thin layer chromatography (silica gel) using $CHCl_3$/MeOH (9:1) as an eluent. 3-Chloro-7-methoxy-IDDC was isolated as a clear yellow syrup (100 mg, 77% yield). $R_f$: 0.36 ($CHCl_3$/MeOH 9:1). $^1$H NMR ($CDCl_3$): δ7.30–6.79 (m, 6H), 4.44 (t, J=3.5 Hz, 1H), 3.86 (d, 1H), 3.85 (s, 3H, $CH_3$), 3.69 (dd, J=12.2 Hz, 1H), 3.56 (dd, J=17.0, 3.3 Hz, 1H), 3.37 (dd, J=13.7, 4.4 Hz, 1H), 3.18 (dd, J=18.5, 4.5 Hz, 1H). $^{13}$C NMR ($CDCl_3$): 159.8, 143.1, 141.2, 132.9, 132.7, 131.5, 128.6, 127.9, 127.3, 127.0, 112.8, 111.7, 55.4, 54.0, 48.8, 45.8, 39.5. High resolution mass spec: $C_{17}H_{16}NClO$ 285.0920 (cal.), 285.0910 (exp.).

H. Synthesis of (±) 3-Fluoro-IDDC

2.-(4-Fluorophenyl)-1-phenyl-1-ethanone.

a) 4-Fluorophenylacetyl chloride: A mixture of 4-fluorophenylacetic acid (8 g, 52 mmol) and phosphorous trichloride (7.13 g, 52 mmol) in a round bottom flask under nitrogen was heated to 95° C. for 1 hour. A mixture of colorless liquid and yellow amorphous solid was formed. The liquid was decanted and used directly for the next step.

b) 2-(4-Fluorophenyl)-1-phenyl-1-ethanone: To a suspension of aluminum chloride (6.927 g, 52 mmol) and in dry benzene (60 ml) under nitrogen was added crude 4-fluorophenylacetyl chloride (approximately 52 mmol) over a period of 30 minutes at room temperature. The resulting clear, pale yellow solution was refluxed for 18 hours. After cooling to room temperature, the resulting solution was poured into 100 ml ice water. The layers were separated and the aqueous portion was extracted with methylene chloride (100 ml, 2 times). The combined organic layers were washed with water (100 ml, 2 times), 10% NaOH (50 ml, 2 times), water (100 ml, 2 times), and brine (40 ml). The organic solution was further dried over $MgSO_4$, filtered, and concentrated to yield the crude product as a white solid (10 g, 98% for two steps). $R_f$: 0.63 ($CH_2Cl_2$). IR ($CH_2Cl_2$) 1700 cm$^{-1}$ (C=O).

2-(4-Fluorophenyl)-1-phenyl-1-ethanone-O-methyl oxime. To a solution of 2-(4-fluorophenyl)-1-phenyl-1-ethanone (5 g, 30 mmol) in 30 ml pyridine under nitrogen was added methoxylamine hydrochloride (3.8 g, 45 mmol) at 25° C. The resulting mixture was stirred at 25° C. for 17 hours. The pyridine was removed in vacuo with heating. The residual solids were a mixture of the oxime geometrical isomers as a white syrup and it was used for the next step without further purification. $R_f$: 0.48, 0.70 ($CH_2C_{12}$).

1-Amino-2-(4-fluorophenyl)-1-phenylethane. To a solution of 2-(4-fluorophenyl)-1-phenyl-1-ethanone-O-methyl oxime (1.34 g, 4.62 mmol) in 30 ml dry THF under nitrogen was added borane-THF complex (1.0M in THF, 23.1 ml, 23.1 mmol) and dry pyridine (10 ml) by syringe at 25° C. The resulting bi-phasic solution was refluxed with vigorous magnetic stirring for 16 hours. After the reaction was cooled to 25° C. and was quenched with 10% NaOH solution, hexanes (50 ml) were added and the layers were separated. The aqueous portion was extracted with hexanes again (40 ml). The combined organic layers were dried over magnesium sulfate and concentrated in vacuo to yield a cloudy colorless syrup (3.55 g, 66% yield for two steps). $R_f$: 0.24 (EtOAc).

1-(N-Ethyl-(2,2-ethoxy))-amino-2-(4-fluorophenyl)-1-phenylethane. To a stirred mixture at 90° C. of 1-amino-2-

(4-fluorophenyl)-1-phenylethane (2.15 g, 10 mmol) and anhydrous potassium carbonate (1.52 g, 11 mmol) in 5 ml of N,N-dimethylformamide were added dropwise a solution of bromoacetaldehyde diethylacetal (2.17 g, 11 mmol). The resulting mixture was heated with stirring. After 18 hours the reaction mixture was cooled to 10° C., 50 ml of 1N NaOH was added followed by 50 ml of $CH_2Cl_2$. The layers were separated and the aqueous layer was extracted with $CH_2Cl_2$ (25 ml, two times). The combined organic layers were washed with NaOH (1N, 20 ml) and water (125 ml, 10 times), dried ($K_2CO_3$), and concentrated to yield the crude product (2.9 g, 88% yield). $R_f$: 0.53 ($CH_2Cl_2$/THF 1:15).

3-Fluoro-IDDC. 1-(N-Ethyl-(2,2-ethoxy))-amino-2-(4-fluorophenyl)-1-phenylethane (100 mg, 1.51 mmol) and perchloric acid (12 ml of 70% solution) were mixed together at room temperature under nitrogen. The resulting white mixture was stirred at room temperature for 48 hour followed by quench and basification with ice and 10% NaOH. The resulting cloudy mixture was extracted with methylene chloride (25 ml, 3 times), and the combined extracts were washed with brine (10 ml) and dried over sodium sulfate. Concentration in vacuo afforded an amber syrup, which was purified by prep. thin layer chromatography (silica gel) using $CHCl_3$/MeOH (9:1) as an eluent. 3-Fluoro-IDDC was isolated as a yellow syrup (175 mg, 49% yield). $R_f$: 0.37 ($CHCl_3$/MeOH 9:1). $^1H$ NMR ($CDCl_3$): δ7.21–6.77 (m, 7H), 4.35 (t, J=3.7 Hz, 1H), 3.84 (d, J=4.2 Hz, 1H), 3.63 (d, J=11.6 Hz, 1H), 3.48 (dd, J=17.4, 3.3 Hz, 1H), 3.25 (dd, J=11.6, 4.8 Hz, 1H), 3.16 (dd, J=17.4, 2.6 Hz, 1H). $^{13}C$ NMR ($CDCl_3$): 142.5 (d, $J_{C-F}$=263.8 Hz), 139.6, 132.9, 132.8, 130.5, 127.5, 127.2, 125.6, 125.1, 114.5 (d, $J_{C-C-F}$= 21.0 Hz), 113.6 (d, $J_{C-C-F}$=20.8 Hz), 54.9, 50.3, 46.6, 40.7. High resolution mass. spec: $C_{16}H_{14}NF$ 239.1110 (cal.), 239.1132 (exp.).

I. Synthesis of (±) 3-Bromo-7-methoxy-IDDC

4-Bromophenylacetyl chloride. A mixture of 4-bromophenylacetic acid (6.45 g, 30 mmol) and phosphorous trichloride (4.12 g, 30 mmol) in a round bottom flask under nitrogen was heated to 50° C., for 30 min, and at 100° C. for 3 hr and then it was allowed to cool to room temperature. A light yellow precipitate appeared after 30 minutes, and the precipitate had congealed into an amorphous yellow solid. The remaining liquid was decanted. The solid was rinsed with methylene chloride (2×5 ml), and the rinses were combined with the decanted liquid. Concentration via rotary evaporation afforded a syrupy pale yellow residue, which was purified by vacuum distillation (short path). The acid chloride was isolated as a clear colorless liquid, (1.804 g 26% yield): b.p. 85°–88° C./0.8 torr.

2-(4-Bromophenyl)-1-(4-methoxyphenyl)-1-ethanone. To a suspension of aluminum chloride (0.97 g, 7.28 mmol) in 40 ml AR dichloromethane under nitrogen was added at room temperature 4-bromophenylacetyl chloride (1.70 g, 7.28 mmol) over a period of 20 minutes as a solution in 15 ml dichloromethane. The resulting clear, off-red solution was refluxed for six hours. After cooling to room temperature, the resulting grey-brown solution was poured into 10 ml ice water. The layers were separated and the aqueous portion extracted with dichloromethane (1×20 ml). The combined organic portions were washed with water (1×30 ml), 10% NaOH (1×30 ml), water (1×30 ml), and brine (1×30 ml), and dried over sodium sulfate. Filtration followed by concentration in vacuo, afforded the ketone as a white crystalline solid (2.14 g, 96% crude yield). This product was used in the next step without any further purification.

2-(4-Bromophenyl)-1-(4-methoxyphenyl)-1-ethanone-O-methyl oxime. To a solution of 2-(4-bromophenyl)-1-(4-methoxyphenyl-1-ethanone 1.987 g, 6.51 mmol) in 20 ml pyridine (anhydrous) under nitrogen was added at room temperature methoxylamine hydrochloride (820 mg, 9.77 mmol). The resulting slightly cloudy, pale orange mixture was stirred at room temperature for 15 hr. The pyridine was removed in vacuo with heating. The residual solids were stirred with ether (60 ml), isolated by filtration, and discarded. The filtrate was dried over sodium sulfate, and concentrated in vacuo to a mixture of the oxime geometrical isomers as a clear, pale yellow syrup, (2.145 g, 98.5% crude yield). This product was used in next step without any further purification.

2-(4-Bromophenyl)-1-(4-methoxyphenyl)-1-amino ethane. To a solution of oxime geometric isomers (2.01 g, 6.01 mmol) in 50 ml anhydrous THF under nitrogen was added borane-tetrahydrofuran complex (1.0M in THF, 30.1 ml, 30.1 mmol) by syringe at room temperature. The resulting pale yellow solution was refluxed 3 hrs, and cooled in an ice bath. Water (25 ml) was carefully added to quench, followed by 20% NaOH (40 ml). the resulting bi-phasic solution was refluxed with vigorous magnetic stirring for 18 hrs. After cooling to room temperature, hexanes (40 ml) were added, and the layers were separated. The aqueous portion was extracted with hexanes (1×40 ml). The combined organic portions were dried over potassium carbonate and concentrated in vacuo to an off-white syrup, (1.913 g, 98.8% crude yield). This product was used in next step without any further purification.

1-(N-ethyl-(2,2-ethoxy))-amino-1-(4-methoxyphenyl)-2-(4-bromophenyl) ethane. To a solution of the amine (1.82 g, 5.65 mmol) in 17 ml anhydrous DMF was added potassium carbonate (859 mg, 6.21 mmol) and bromoacetaldehyde diethylacetal (1.22 g, 6.21 mmol, Aldrich, used as is) at room temperature under nitrogen. The resulting clear colorless suspension was heated at 100° C. for 32 hours. After cooling to room temperature, the reaction mixture was mixed with 10% NaOH (100 ml). The resulting yellow cloudy mixture was extracted with methylene chloride (3×50 ml). The combined organic portions were washed with 1N NaOH solution (1×30 ml), water (1×30 ml) and brine (1×30 ml), dried over potassium carbonate. Concentration in vacuo afforded a light orange liquid that was purified by flash chromatography on silica gel, using 8:2 hexanes/ethyl acetate as eluant. The acetal was isolated as a colorless syrup, which solidified in refrigerator to give an off-white solid, (2.1 g, 87.8% yield).

(±) 3-Bromo-7-methoxy-IDDC. The acetal (1.032 g, 2.44 mmol) and perchloric acid (20 g of a 69% solution) were mixed together at room temperature under nitrogen. The resulting light-brown mixture was stirred at room temperature for 52 hours, followed by quench and basification with ice and 10% NaOH (100 ml). The resulting cloudy mixture was extracted with methylene chloride (3×50 ml), and the combined extracts were washed with 2N aq. NaOH solution (1×50 ml), water (17.50 ml), brine (1×50 ml) and dried over potassium carbonate. Concentration in vacuo afforded an amber syrup, which was purified by flash chromatography on silica gel using 10:1 chloroform/methanol as eluent. The 3-bromo-7-methoxy-IDDC was isolated as a shiny white solid, (0.516 g, 64% yield). $^1H$ NMR ($CDCl_3$): δ7.34–6.73 (m, 6H), 4.33(t, J=3.4 Hz, 1H), 3.79 (d, 1H), 3.79 (s, 3H, $CH_3$), 3.61 (d, J=11.7 Hz, 1H), 3.43 (dd, J=17.7, 3.6 Hz, 1H), 3.28 (dd, J=11.5, 4.6 Hz, 1H), 3.11 (dd, J=17.7, 3.2 Hz, 1H). $^{13}C$ NMR ($CDCl_3$): 159.1, 144.7, 141.9, 134.4, 133.2, 131.9, 130.7, 129.8, 126.2, 119.4, 112.3, 111.6, 55.4, 54.0, 50.1, 46.8, 41.4. High resolution mass. spec: $Cl_7H_{16}NBrO$ 329.0415 (cal.), 329.0428 (exp.).

J. Synthesis of (±) N-Methyl-3-bromo-7-methoxy-IDDC

To a solution of 3-bromo-7-methoxy-IDDC (50 mg, 0.15 mmol) in 1.1 ml of formic acid under nitrogen was added formaldehyde (37% aqueous solution, 0.061 ml, 0.758 mmol) at room temperature. The reaction mixture was stirred at room temperature for three hours and further refluxed for two hours. The resulting solution was basified with aqueous NaOH (1N) to pH 12 and extracted with methylene chloride (40 ml, two times). The organic extracts were combined, dried (MgSO$_4$), filtered, and concentrated to yield the crude product. The crude product was purified by prep. thin layer chromatography (silica gel) using CHCl$_3$/MeOH (9:1) as an eluent. N-Methyl-3-bromo-7-methoxy-IDDC was isolated as a yellow syrup (42 mg, 78% yield). $^1$H MNR (CDCl$_3$): δ7.31–6.75 (m, 6H), 3.93–3.74 (m, 2H), 3.79 (s, 3H, CH$_3$), 3.60–3.53 (m, 2H), 2.94–2.85 (m, 2H), 2.49 (s, 3H, CH$_3$). $^{13}$C NMR (CDCl$_3$): 159.2, 144.2, 141.9, 134.4, 133.0, 130.5, 130.3, 129.8, 127.1, 119.2, 112.2, 111.2, 61.8, 59.3, 55.4, 46.9, 45.3, 38.6. High resolution mass spec: C$_{18}$H$_{18}$BrNO 343.0571 (cal.), 343.0564 (exp.).

K. Synthesis of (±) 3-Iodo-IDDC

The method of Thompson et al. was followed (Thompson, W. T. et al *J. Med. Chem.* 33:789–808 (1990); see also Takagi, K.; Hayama, N.; Okamoto, T. *Chem. Lett.* p. 191 (1978)). A mixture of 3-bromo-IDDC (75 mg, 0.25 mmol), nickel powder (73 mg, 1.3 mmol, Aldrich, 3 micron particle size), potassium iodide (83 mg, 0.50 mmol), iodine (3 mg, 0.01 mmol) and DMF (0.50 ml, dried over molecular sieves) was degassed by bubbling nitrogen through for 20 minutes. A septum was placed on the flask with a nitrogen inlet, and the flask was immersed in an oil bath at 150° C. After 5 hours of stirring, the heat was removed and the reaction mixture allowed to achieve room temperature. Water (5 ml) and ethyl acetate (5 ml) were added with stirring. The liquid portion was removed by pipette, and the residual solids rinsed with ethyl acetate (3×5 ml). All the liquids were combined and hexanes (10 ml) were added. The layers were separated and the organic portion was dried over sodium sulfate. The solvent was evaporated to afford a clear brown syrup, which was purified by flash chromatography using an elution gradient of 100% ethyl acetate to 10% methanol (containing 1% concentrated ammonium hydroxide) in ethyl acetate. A pale yellow, cloudy syrup was obtained (46.6 mg); proton NMR analysis indicated that this syrup was a mixture of 85% product (3-iodo-IDDC) and 15% starting material (3-bromo-IDDC). This mixture was subjected to the same reaction conditions with fresh reagents to yield material of the same product/starting material ratio (46% yield after the first reaction): R$_f$ 0.23 (20% methanol/ethyl acetate); $^1$H NMR (acetone-d$_6$) δ7.62 (d, J=1.5 Hz, 1H), 7.40 (dd, J=8.2, 1.6 Hz, 1H), 7.29–7.10 (m, 4H), 6.81 (d, J=8.1 Hz, 1n), 4.35 (t, J=3.5 Hz, 1H), 3.97 (d, J=3.7 Hz, 1H), 3.51 (dd, J=10.7, 0.9 Hz, 1H), 3.36 (dd, J=17.7, 3.6 Hz, 1H), 3.23 (dd, J=11.3, 4.7 Hz, 1H), 3.03 (dd, J=17.7, 3.2 Hz, 1H); 1.26 (s, 1H).

L. Synthesis of (−)-3-Chloro-IDDC

To a solution of (±)-3-chloro-IDDC (484.3 mg, 1.894 mmol) in 1.40 ml methyl ethyl ketone at 50° C. was added a warm solution of (+)-di-p-toluoyl-D-tartaric acid monohydrate (772 mg, 1.91 mmol) with stirring. A white precipitate formed immediately. The reaction flask was fitted with a condenser and the reaction mixture stirred under nitrogen at 50° C. for 48 hours. The precipitated salt was collected on a Hirsch funnel and rinsed with cold acetone. The precipitate (1.0368 g of a pale brown powder; m.p. 174–176 dec.; [α]$_D^{25}$=70° C., c=1, MeOH) was subjected to recrystallization conditions using boiling methyl ethyl ketone, methanol (20:1); however, solid formation was not realized. The solvent was evaporated, and the salt was partitioned between methylene chloride (20 ml) and 4M NH$_4$OH (20 ml). The layers were separated and the aqueous portion extracted with methylene chloride (2×15 ml). The combined organic portions were dried over potassium carbonate and concentrated in vacuo to yield the free base (i.e., 3-chloro-IDDC) as a clear brown syrup. This cycle was completed twice more, each time using 1.02 equivalents of the tartaric acid relative to the free base, stirring in methyl ethyl ketone or 48 hours at 50° C. followed by regeneration of the free base, to yield (−)-3-chloro-IDDC as 94 mg of a clear, colorless syrup (unoptimized). R$_f$ 0.17 (ethyl acetate/methanol 4:1); [α]$_D^{25}$= −144° (c=1, EtOH); $^1$H NMR (CDCl$_3$) δ7.26–7.18 (m, 5H), 7.08 (dd, J=8.1, 2.1 Hz, 1H), 6.97 (d, J=8.2 Hz, 1H), 4.32 (t, J=3.7 Hz, 1H), 3.87 (d, J=4.5 Hz, 1H), 3.65 (d, J=11.7 Hz, 1H), 3.45 (dd, J=17.6, 3.8 Hz, 1H), 3.32 (dd, J=11.5, 4.8 Hz, 1H), 3.17 (dd, J=17.6, 3.4 Hz, 1H), 1.99 (s, 1H).

Example 10
PCP Binding Data for IDDC Analogs

The PCP receptor affinities of the IDDC analogs against [$^3$H]MK-801 synthesized above were determined as described by Keana F. W. et al., *Proc. Natl. Acad. Sci. (USA)* 86:5631–5635 (1989). The results appear in Table 2.

As can be seen in Table 2, the IDDC analogs of the invention exhibit high binding to the PCP receptor.

| BINDING DATA FOR IDDC ANALOGS | | |
|---|---|---|
| | PCP Receptor Affinity IC$_{50}$ (nM) in Rat Brain Membrane vs. [$^3$H]MK-801 | |
| Compound | MEAN | ±SEM (n) |
| (±)-IDDC | 74.6 | 10.2(2) |
| (+)-IDDC | 40.0 | 5.0(4) |
| (+)-N—Me-IDDC | 65.4 | 9.5(3) |
| (±)-3-Cl-IDDC | 64.2 | 8.0(2) |
| (±)-7-OMe-IDDC | 331.5 | (2) |
| (±)-5-Me-IDDC | 118.8 | 17.0(5) |
| (±)-3-Br-IDDC | 41.0 | 4.5(3) |
| (±)-3-Cl-7-OMe-IDDC | 113.0 | 26.0(4) |
| (±)-3-Br-7-OMe-IDDC | 114.0 | 24.0(3) |
| (±)-7-Cl-IDDC | 690.0 | 108.0(3) |
| (±)-3-NH2-IDDC | 486.0 | 86.0(3) |
| (±)-3-Br—N—Me-IDDC | 1,044.0 | 146.0(3) |
| (±)-3-Br-7-OMe—N—Me-IDDC | 643.0 | 209.0(2) |
| (±)-3-F-IDDC | 29.4 | 0.9(3) |
| (±)-3-OMe-IDDC | 168.0 | 2.0(2) |
| (±)-3-Iodo-IDDC | 160.0 | 16.0(2) |
| (−)-3-Chloro-IDDC | 110.0 | 2.0(2) |
| (+)-3-Fluoro-IDDC | 18 | |
| (+)-3-Chloro-IDDC | 14 | |

Having now fully described this invention, it will be understood to those of ordinary skill in the art that the same can be performed within a wide and equivalent range of conditions, formulations and other parameters without affecting the scope of the invention or any embodiment thereof.

What is claimed is:

1. A compound selected from the group consisting of
   3-chloro-5-(iminomethano)-10,11-dihydro-5H-dibenzo [a,d]cycloheptene;

(+) 3-chloro-5-(iminomethano)-10,11-dihydro-5H-dibenzo[a,d]cycloheptene;

7-methoxy-5-(iminomethano)-10,11-dihydro-5H-dibenzo [a,d]cycloheptene;

3-bromo-5-(iminomethano)-10,11-dihydro-5H-dibenzo[a,d]cycloheptene;

3-chloro-7-methoxy-5-(iminomethano)-10,11-dihydro-5H-dibenzo[a,d]cycloheptene;

3-bromo-7-methoxy-5-(iminomethano)-10,11-dihydro-5H-dibenzo[a,d]cycloheptene;

7-chloro-5-(iminomethano)-10,11-dihydro-5H-dibenzo[a,d]cycloheptene;

3-bromo-7-amino-5-(iminomethano)-10,11-dihydro-5H-dibenzo[a,d]cycloheptene;

3-bromo-7-methoxy-N-methyl-5-(iminomethano)-10,11-dihydro-5H-dibenzo[a,d]cycloheptene;

3-fluoro-5-(iminomethano)-10,11-dihydro-5H-dibenzo[a,d]cycloheptene;

(+)3-fluoro-5-(iminomethano)-10,11-dihydro-5H-dibenzo[a,d]cycloheptene;

3-methoxy-5-(iminomethano)-10,11-dihydro-5H-dibenzo[a,d]cycloheptene;

3-iodo-5-(iminomethano)-10,11-dihydro-5H-dibenzo[a,d]cycloheptene;

(−)-3-chloro-5-(iminomethano)-10,11-dihydro-5H-dibenzo[a,d]cycloheptene;

(±)-N-methyl-3-fluoro-5-(iminomethano)-10,11-dihydro-5H-dibenzo[a,d]cycloheptene;

(+)-N-methyl-3-fluoro-5-(iminomethano)-10,11-dihydro-5H-dibenzo[a,d]cycloheptene;

(±)-N-methyl-3-chloro-5-(iminomethano)-10,11-dihydro-5H-dibenzo[a,d]cycloheptene;

(+)-N-methyl-3-chloro-5-(iminomethano)-10,11-dihydro-5H-dibenzo[a,d]cycloheptene;

3-nitro-5-(iminomethano)-10,11-dihydro-5H-dibenzo-[a,d]cycloheptene;

3-azido-5-(iminomethano)-10,11-dihydro-5H-dibenzo-[a,d]cycloheptene;

3-trifluoromethyl-5-(iminomethano)-10,11-dihydro-5H-dibenzo-[a,d]cycloheptene;

N-methyl-3-trifluoromethyl-5-(iminomethano)-10,11-dihydro-5H-dibenzo-[a,d]cycloheptene;

3,7-difluoro-5-(iminomethano)-10,11-dihydro-5H-dibenzo-[a,d]cycloheptene;

3-phenyl-5-(iminomethano)-10,11-dihydro-5H-dibenzo-[a,d]cycloheptene;

3-amino-5-(iminomethano)-10,11-dihydro-5H-dibenzo-[a,d]cycloheptene;

8-hydroxy-5-(iminomethano)-10,11-dihydro-5H-dibenzo-[a,d]cycloheptene;

3-hydroxy-5-(iminomethano)-10,11-dihydro-5H-dibenzo-[a,d]cycloheptene;

8-methoxy-5-(iminomethano)-10,11-dihydro-5H-dibenzo-[a,d]cycloheptene;

3-cyano-5-(iminomethano)-10,11-dihydro-5H-dibenzo-[a,d]cycloheptene;

3-methylthio-5-(iminomethano)-10,11-dihydro-5H-dibenzo-[a,d]cycloheptene;

(+)-5-(iminomethano)-10,11-dihydro-5H-dibenzo[a,d]cycloheptene;

N-methyl-5-(iminomethano)-10,11-dihydro-5H-dibenzo[a,d]cycloheptene; and

N-methyl-3-iodo-5-(iminomethano)-10,11-dihydro-5H-dibenzo-[a,d]cycloheptene;

or a pharmaceutically acceptable salt thereof and/or the optically active isomer thereof.

2. A method of treating or preventing neuronal loss, comprising administering to an animal in need of such treatment an effective amount of a compound of claim 1.

3. The method of claim 2, wherein said neuronal loss is associated with ischemia, stroke heart attack, hypoxia, hypoglycemia, brain or spinal cord trauma, Alzheimer's disease, amyotrophic lateral sclerosis, Huntington's disease or Down's syndrome.

4. The method of claim 2, wherein said animal is a human suffering from ischemic brain insult and said compound is administered as part of a pharmaceutical composition comprising a pharmaceutically acceptable carrier.

5. The method of claim 2, wherein said compound is administered as part of a pharmaceutical composition comprising a pharmaceutically acceptable carrier.

6. A method of inhibiting NMDA receptor-ion channel related neurotoxicity comprising administering to an animal in need of such treatment an effective amount of a compound of claim 2.

7. The method according to claim 6, wherein said neurotoxicity is caused by excessive release of endogenous glutamate following ischemic brain insult.

8. The method of claim 6, wherein said animal is a human suffering from ischemic brain insult.

9. The method of claim 7, wherein said compound is administered as part of a pharmaceutical composition comprising a pharmaceutically acceptable carrier.

10. 3-Chloro-5-(iminomethano)-10,11-dihydro-5H-dibenzo-[a,d]cycloheptene, a compound of claim 1.

11. (+) 3-Chloro-5-(iminomethano)-10,11-dihydro-5H-dibenzo-[a,d]cycloheptene, a compound of claim 1.

12. 7-Methoxy-5-(iminomethano)-10,11-dihydro-5H-dibenzo-[a,d]cycloheptene, a compound of claim 1.

13. 3-Bromo-5-(iminomethano)-10,11-dihydro-5H-dibenzo-[a,d]cycloheptene, a compound of claim 1.

14. 3-Fluoro-5-(iminomethano)-10,11-dihydro-5H-dibenzo-[a,d]cycloheptene, a compound of claim 1.

15. (+) 3-Fluoro-5-(iminomethano)-10,11-dihydro-5H-dibenzo-[a,d]cycloheptene, a compound of claim 1.

16. 3-Methoxy-5-(iminomethano)-10,11-dihydro-5H-dibenzo-[a,d]cycloheptene, a compound of claim 1.

17. 3-Iodo-5-(iminomethano)-10,11-dihydro-5H-dibenzo-[a,d]cycloheptene, a compound of claim 1.

18. N-methyl-3-fluoro-5-(iminomethano)-10,11-dihydro-5H-dibenzo-[a,d]cycloheptene, a compound of claim 1.

19. N-methyl-3-fluoro-5-(iminomethano)-10,11-dihydro-5H-dibenzo-[a,d]cycloheptene, a compound of claim 1.

20. A method of treating neuronal loss, comprising administering to a mammal in need of such treatment an effective of 3-chloro-5-(iminomethano)-10, 11-dihydro-5H-dibenzo[a,d]cycloheptene;

(+) 3-chloro-5-(iminomethano)-10,11-dihydro-5H-dibenzo-[a,d]cycloheptene;

7-methoxy-5-(iminomethano)-10,11-dihydro-5H-dibenzo-[a,d]cycloheptene;

3-bromo-5-(iminomethano)-10,11-dihydro-5H-dibenzo-[a,d]cycloheptene;

3-fluoro-5-(iminomethano)-10,11-dihydro-5H-dibenzo-[a,d]cycloheptene;

(+) 3-fluoro-5-(iminomethano)-10,11-dihydro-5H-dibenzo-[a,d]cycloheptene;

3-methoxy-5-(iminomethano)-10,11-dihydro-5H-dibenzo-[a,d]cycloheptene;

3-iodo-5-(iminomethano)-10,11-dihydro-5H-dibenzo-[a,d]cycloheptene; or

N-methyl-3-fluoro-5-(iminomethano)-10,11-dihydro-5H-dibenzo-[a,d]cycloheptene; or a pharmaceutically acceptable salt thereof.

21. The method of claim 20 wherein the neuronal loss is associated with ischemia, stroke, heart attack, hypoxia, hypoglycemia, brain or spinal cord trauma, Alzheimer's disease, amyotrophic lateral sclerosis, Huntington's disease or Down's syndrome.

22. A method of treating a mammal suffering from ischemia, stroke, heart attack, hypoxia, hypoglycemia or brain or spinal cord trauma, comprising administering to the mammal an effective amount of

- 3-chloro-5-(iminomethano)-10,11-dihydro-5H-dibenzo-[a,d]cycloheptene;
- (+) 3-chloro-5-(iminomethano)-10,11-dihydro-5H-dibenzo-[a,d]cycloheptene;
- 7-methoxy-5-(iminomethano)-10,11-dihydro-5H-dibenzo-[a,d]cycloheptene;
- 3-bromo-5-(iminomethano)-10,11-dihydro-5H-dibenzo-[a,d]cycloheptene;
- 3-fluoro-5-(iminomethano)-10,11-dihydro-5H-dibenzo-[a,d]cycloheptene;
- (+) 3-fluoro-5-(iminomethano)-10,11-dihydro-5H-dibenzo-[a,d]cycloheptene;
- 3-methoxy-5-(iminomethano)-10,11-dihydro-5H-dibenzo-[a,d]cycloheptene;
- 3-iodo-5-(iminomethano)-10,11-dihydro-5H-dibenzo-[a,d]cycloheptene; or
- N-methyl-3-fluoro-5-(iminomethano)-10,11-dihydro-5H-dibenzo-[a,d]cycloheptene; or a pharmaceutically acceptable salt thereof.

23. A method of treating a mammal suffering from Alzheimer's disease, amyotrophic lateral sclerosis, Huntington's disease or Down's syndrome, comprising administering to the mammal an effective amount of

- 3-chloro-5-(iminomethano)-10,11-dihydro-5H-dibenzo-[a,d]cycloheptene;
- (+) 3-chloro-5-(iminomethano)-10,11-dihydro-5H-dibenzo-[a,d]cycloheptene;
- 7-methoxy-5-(iminomethano)-10,11-dihydro-5H-dibenzo-[a,d]cycloheptene;
- 3-bromo-5-(iminomethano)-10,11-dihydro-5H-dibenzo-[a,d]cycloheptene;
- 3-fluoro-5-(iminomethano)-10,11-dihydro-5H-dibenzo-[a,d]cycloheptene;
- (+) 3-fluoro-5-(iminomethano)-10,11-dihydro-5H-dibenzo-[a,d]cycloheptene;
- 3-methoxy-5-(iminomethano)-10,11-dihydro-5H-dibenzo-[a,d]cycloheptene;
- 3-iodo-5-(iminomethano)-10,11-dihydro-5H-dibenzo-[a,d]cycloheptene; or
- N-methyl-3-fluoro-5-(iminomethano)-10,11-dihydro-5H-dibenzo-[a,d]cycloheptene; or a pharmaceutically acceptable salt thereof.

* * * * *